United States Patent
Kohr

(10) Patent No.: US 10,378,009 B2
(45) Date of Patent: Aug. 13, 2019

(54) MICROBIAL ENHANCED OIL RECOVERY METHODS UTILIZING A MICROORGANISM THAT IS DEFICIENT IN ITS ABILITY TO DEGRADE SHORT CHAIN HYDROCARBONS

(71) Applicant: GEO FOSSIL FULES, LLC, Houston, TX (US)

(72) Inventor: William J. Kohr, Gig Harbor, WA (US)

(73) Assignee: GEO FOSSIL FUELS, LLC, Houston, TX (US)

( * ) Notice: Subject to any disclaimer, the term of this patent is extended or adjusted under 35 U.S.C. 154(b) by 0 days.

(21) Appl. No.: 15/171,927

(22) Filed: Jun. 2, 2016

(65) Prior Publication Data

US 2016/0272962 A1  Sep. 22, 2016

Related U.S. Application Data

(60) Continuation of application No. 13/656,294, filed on Oct. 19, 2012, now abandoned, which is a division of application No. 12/869,647, filed on Aug. 26, 2010, now Pat. No. 8,316,933.

(60) Provisional application No. 61/238,044, filed on Aug. 28, 2009.

(51) Int. Cl.
| | |
|---|---|
| C12N 9/02 | (2006.01) |
| C12N 15/10 | (2006.01) |
| C09K 8/582 | (2006.01) |
| C12N 1/26 | (2006.01) |
| E21B 43/16 | (2006.01) |
| C12N 1/00 | (2006.01) |
| C12N 1/20 | (2006.01) |

(52) U.S. Cl.
CPC ............ *C12N 15/102* (2013.01); *C09K 8/582* (2013.01); *C12N 1/00* (2013.01); *C12N 1/20* (2013.01); *C12N 1/26* (2013.01); *C12N 9/0077* (2013.01); *E21B 43/16* (2013.01); *C12Y 114/15003* (2013.01)

(58) Field of Classification Search
None
See application file for complete search history.

(56) References Cited

U.S. PATENT DOCUMENTS

| | | | |
|---|---|---|---|
| 2,413,278 A | 12/1946 | Zobell | |
| 5,013,564 A | 5/1991 | Banerjee et al. | |
| 5,037,758 A | 8/1991 | Mulligan et al. | |
| 5,297,625 A | 3/1994 | Premuzic et al. | |
| 6,030,779 A | 2/2000 | Short | |
| 6,896,054 B2 | 5/2005 | McClung | |
| 7,033,781 B1 * | 4/2006 | Short .................. | C12N 15/102 435/6.16 |
| 8,316,933 B2 * | 11/2012 | Kohr ...................... | C09K 8/582 166/246 |
| 9,259,662 B2 * | 2/2016 | Lee ....................... | B01D 1/0035 |
| 9,290,688 B2 * | 3/2016 | Kohr ...................... | C09K 8/582 |
| 9,869,166 B2 * | 1/2018 | Kohr ...................... | C09K 8/582 |
| 10,227,853 B2 * | 3/2019 | Kohr ...................... | C09K 8/582 |
| 2004/0077090 A1 * | 4/2004 | Short .................... | C12N 15/102 506/1 |
| 2009/0238044 A1 * | 9/2009 | Satoh ...................... | H02P 8/38 368/155 |
| 2011/0067856 A1 * | 3/2011 | Kohr ...................... | C09K 8/582 166/246 |
| 2012/0115201 A1 | 5/2012 | Adams | |
| 2012/0141384 A1 * | 6/2012 | Tamarkin ............... | A61K 31/69 424/45 |
| 2013/0062053 A1 * | 3/2013 | Kohr ...................... | C09K 8/582 166/246 |
| 2014/0051149 A1 * | 2/2014 | Kohr ...................... | C09K 8/582 435/252.1 |
| 2016/0152943 A1 * | 6/2016 | Kohr ...................... | C09K 8/582 435/252.3 |
| 2016/0222280 A1 * | 8/2016 | Kohr ...................... | C09K 8/582 |
| 2016/0272962 A1 * | 9/2016 | Kohr ...................... | C09K 8/582 |
| 2018/0112504 A1 * | 4/2018 | Kohr ...................... | C09K 8/582 |

FOREIGN PATENT DOCUMENTS

| | | | | |
|---|---|---|---|---|
| CA | 2772395 A1 * | 3/2011 | ............ | C09K 8/582 |
| GB | 2222420 | 3/1990 | | |
| WO | WO-2011025984 A1 * | 3/2011 | ............ | C09K 8/582 |
| WO | WO-2012116230 A1 * | 8/2012 | ............ | C09K 8/582 |

OTHER PUBLICATIONS

Vargas et al, Genetic Tools for the Manipulation of Moderately Halophilic Bacteria of the Family Halomonadaceae, Methods in Molecular Biology, vol. 267:183-208. 2004, Recombinant Gene Expression: Reviews and Protocols, Second Edition Edited by: P. Balbás and A. Lorence © Humana Press Inc., Totowa, NJ (Year: 2004).*
Belyaev et al, Halotolerant and Extremely Halophilic Oil-Oxidizing Bacteria in Oil Fields, Microbial Enhancement of Oil Recovery—Recent Advances [4th US Doe Meor Int. Conf. (Upton, NY, 1992). abstract only (Year: 1992).*
Kelly A. Bidle, Differential expression of genes influenced by changing salinity using RNA arbitrarily primed PCR in the archaeal halophile Haloferax volcanii. Extremophiles, 2003, 7:1-7, published online: Sep. 3, 2002 (Year: 2003).*
Ghojavand et al, Isolation of thermotolerant, halotolerant, facultative biosurfactant-producing bacteria. Appl. Microbiol. Biotechnol, 2008, 80:1073-1085, published online: Aug. 6, 2008 (Year: 2008).*
Lee et al, Identification of a novel protein D3UPCA from Halobacterium salinarum and prediction of its function. Proteomics, 2004, 4:3622-3631 (Year: 2004).*

(Continued)

*Primary Examiner* — Nita M. Minnifield
(74) *Attorney, Agent, or Firm* — Benjamin C. Pelletier; Alissa H. Faris; Venable, LLP

(57) ABSTRACT

Aspects of the invention include methods and compositions for microbial enhanced oil recovery (MEOR). In particular, the invention focuses on new, efficient, economical and environmentally safe microbial methods to enhance oil recovery in existing oil reservoirs, as well as microorganisms useful in such methods.

16 Claims, 3 Drawing Sheets

Specification includes a Sequence Listing.

(56) References Cited

OTHER PUBLICATIONS

Margesin et al, Potential of halotolerant and halophilic microorganisms for biotechnology. Extremophiles, 2001, 5:73-83, published online: Apr. 7, 2001 (Year: 2001).*
Zhao et al, Biotechnological applications of moderately halophilic eubacteria. Weishengwuxue Tongbao (2007), 34(2), 359-362, abstract only (Year: 2007).*
Amleida et al, Selection and Application of Microorganisms to Improve Oil Recovery. ENg. Life Sci., 2004, 4/4:319-325 (Year: 2004).*
Brown, Microbial enhanced oil recovery (MEOR). Current Opinion in Microbiology, 2010, 13:316-320, available online Feb. 9, 2010 (Year: 2010).*
Patel et al. Recent developments in microbial enhanced oil recovery. Renewable and Sustainable Energy Reviews, 2015, 52:1539-1558. available online Aug. 29, 2015 (Year: 2015).*
Allers, et al., "Archaea genetics—the third way," Nature 2005, 6:58-73.
Allers, et al., "Development of additional selectable markers for the halophilic archaeon haloferax volcanii based on the LeuB and trpA genes," Applied and Environmental Microbiology, pp. 943-953, (2004).
Anton, et al., "Production of an Extracellular polysaccharide by haloferax mediterranei," Applied and Environmental Microbiology, pp. 2381-2386, (1988).
Berquist, et al., "Genetic systems for Halophilic Archaea," Methods in Microbiology, vol. 35, pp. 649-680, (2006).
Bitan-Banin, et al., "Development of a Gene knockout system for the halophilic archaeon haloferax volcanii by use of the pyrE Gene," Journal of Bacteriology, vol. 185, No. 3, pp. 772-778, (2003).
Bodour, et al., "Application of a modified drop-collapse technique for surfactant quantitation and screening of biosurfactant-producing microorganisms," Journal of Microbiological Methods, 32: 273-280, (1998).
Brzostowicz, et al., "Simultaneous identification of two cyclohexanone oxidation genes from an environmental brevibacterium isolate using mRNA differential display," Journal of Bacteriology, pp. 4241-4248, (2000).
Cayol, et al., "Isolation and characterization of *Halothermothrix orenii* gen. nov., sp. Nov., a halophilic, thermophilic, fermentative, strictly anaerobic bacterium," International Journal of Systemic Bacteriology, pp. 534-540, (1994).
Chuang, et al., "Characterization of twenty-six new heat shock genes of *Escherichia coli*," Journal of Bacteriology, pp. 5242-5252, (1993).
Cooper, et al., "Enhanced production of surfactin from bacillus subtilis by continuous product removal and metal cation additions," Applied and Environmental Microbiology, pp. 408-412, (1981).
Dinamarca, et al., "Expression of the pseudomonas putida OCT plasmid alkane degradation pathway is modulated by two different global control signals. evidence from continuous cultures," Journal of Bacteriology, pp. 4772-4778, (2003).
Ebel, et al., "Solvent interactions of halophilic Malate dehydrogenase," Biochemistry, 41: 13234-13244, (2002).
Enache, et al., "Phylogenetic relationships within the family Halobacteriaceae inferred from rpoB' gene and protein sequences," International Journal of Systematic and Evolutionary Microbiology, 57: 2289-2295, (2007).
Feng, et al., "Genome and proteome of long-chain alkane degrading Geobacillus thermodenitrificans NG80-2 isolated from a deep-subsurface oil reservoir," PNAS, vol. 104, No. 13, pp. 5602-5607, (2007).
Fire, et al., "Potent and specific genetic interference by double-stranded RNA in Caenorhabditis elegans," Nature, vol. 39, pp. 806-811, (1998).
Fukuchi, et al., "Unique amino acid composition of proteins in halophilic bacteria," Journal of Molecular Biology, 327: 347-357, (2003).
Gray, et al., "Molecular mechanisms of biocatalytic desulfurization of fossil fuels," Nature Biotechnology, vol. 14, pp. 1705-1709, (1996).
Guerra-Santos, et al., "Dependence of pseudomonas aeruginosa continuous culture biosurfactant production on nutritional and environmental factors," Appl. Microbiol. Biotechnol., 24: 443-448, (1986).
Jain, et al., "A drop-collapsing test for screening surfactant-producing microorganisms," Journal of Microbiological Methods, 13: 271-279, (1991).
Javaheri, et al., "Anaerobic production of a biosurfactant by bacillus licheniformis JF-2," Applied and Environmental Microbiology, pp. 698-700, (1985).
Jennerman, et al., "Experimental studies of in-situ microbial enhanced oil recovery," Society of Petroleum Engineers Journal, pp. 33-37, (1984).
Jennings, et al., "Biocurfactant-producing bacteria found in contaminated and uncontaminated coils," Proceedings of the 2000 conference on Hazardous Waste Research, p. 299-306, (2000).
Kaiser, et al., "Microbial metabolism of pyridine, quinoline, acridine, and their derivatives under aerobic and anaerobic conditions," Microbiology Reviews, pp. 483-498, (1996).
Kebbouche-Gana, et al., "Isolation and characterization of halophilic archaea able to produce biosurfactants," J. Ind. Microbiol. Biotechnol., 36: 727-738, (2009).
Lang, et al., "Rhamnose lipids—biosynthesis, microbial production and application potential," Appl. Microbiol. Biotechnol., 51: 22-32, (1999).
Li, et al., "Crystal structure of long-chain alkane monooxygenase (LasA) in complex with coenzyme FMN: Unveiling the long-chain alkane hydroxylase," Journal of Molecular Biology, 376: 453-465, (2008).
Madem, et al., "Insights into the molecular relationships between Malate and Lactate Dehydrogenases: Structural and biochemical properties of monomeric and dimeric intermediates of a mutant of Tetrameric 1-(LDH-like) Malate dehydrogenase from the halophilic archaeon haloarcula marismortui," Biochemistry, 39: 1001-1010, (2000).
Manikandan et al., "Optimization of growth media for obtaining high-cell density cultures of halophilic archaea (family halobacteriaceae) by response surface methodology," Bioresource Tech., 2009, 100:3107,3112.
Minz, et al., "Diversity of sulfate-reducing bacteria in oxic and anoxic regions of a microbial mat characterized by comparative analysis of dissimilatory sulfite reductase genes," Applied and Environmental Microbiology, pp. 4666-4671, (1999).
Montalvo-Rodriquez, et al., "*Halogeometricum borinquense* gen. nov., sp. Nov., a novel halophilic archaeon from Puerto Rico," International Journal of Systematic Bacteriology, 48: 1305-1312, (1998).
Nuttall, et al., "The ShBle resistance determinant from Streptoalloteichus hindustanus is expressed in haloferax volcanii and confers resistance to bleomycin," Biochem J., 251-254, (2000).
Oren, et al., "*Haloarcula quadrata* sp. Von., a square, motile archaeon isloated from a brine pool in Sinai (Egypt)," International Journal of Systematic Bacteriology, 49: 1149-1155, (1999).
Paul, et al., "Molecular signature of hypersaline adaptation: insights from genome and proteome composition of halophilic prokaryotes," Genome Biology, 9: R70-R70.19, (2008).
Pepi, et al., "An antarctic psychrotrophic bacterium *Halomonas* sp. ANT-3b, growing on n-hexadecane, produces a new emulsifying glycolipid," FEMS Microbiology Ecology, vol. 53, pp. 157-166 (2005).
Pfiffner, et al., "Isolation of halotolerant, thermotolerant, facultative polymer-producing bacteria and characterization of the exopolymer," Applied and Environmental Microbiology, pp. 1224-1229, (1986).
Reuter, et al., "Analysis of proteasome-dependent proteolysis in haloferax volcanii cells, using short-lived green fluorescent proteins," Applied and Environmental Microbiology, vol. 70, No. 12, pp. 7530-7538, (2004).
Sato, et al., "Cloning of genes involved in carbazole degradation of *Pseudomonas* sp. Strain CA10: nucleotide sequences of genes and characterization of meta-cleavage enzymes and hydrolase," Journal of Bacteriology, pp. 4841-4849, (1997).

(56) References Cited

OTHER PUBLICATIONS

Schneiker, et al., "Genome sequence of the ubiquitous hydrocarbon-degrading marine bacterium Alcanivorax borkumensis," Nature Biotechnology, vol. 24, No. 8, pp. 997-1004, (2006).
Supplemental: NCBI Accession No. AY291460.1 Natural plasmids and plasmid vectors of halophiles (Jun. 5, 2003).
Tadeo, et al., "Structural basis for the amino acid composition of proteins from halophilic archea," PLOS Biology, vol. 7, Issue 12, pp. 1-9, (2009).
Throne-Holst, et al., "Identification of novel genes involved in long-chain n-Alkane degrading by *Acinetobacter* sp. Strain DSM 17874," Applied and Environmental Microbiology, pp. 3327-3332, (2007).
Tomlinson, et al., "*Halobacterium denitrificans* sp. Nov., an extremely halophilic denitrifying bacterium," International Journal of Systemic Bacteriology, vol. 36, No. 1, pp. 66-70, (1986).
Wang, et al., "Arsenic resistance in *Halobacterium* sp. Strain NRC-1 examined by using an improved gene knockout system," Journal of Bacteriology, pp. 3187-3194, (2004).
Whyte, et al., "Gene cloning and characterization of multiple alkane hydroxylase systems in rhodococcus strains Q15 and NRRL B-16531," Applied and Environmental Microbiology, pp. 5933-5942, (2002).

\* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ttccggttga tccygccgga                                                   20

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 2
yccggcgttg amtccaatt                     19

<210> SEQ ID NO 3
<211> LENGTH: 440
<212> TYPE: PRT
<213> ORGANISM: Geobacillus thermodenitrificans

<400> SEQUENCE: 3

```
Met Thr Lys Lys Ile His Ile Asn Ala Phe Glu Met Asn Cys Val Gly
1               5                   10                  15

His Ile Ala His Gly Leu Trp Arg His Pro Glu Asn Gln Arg His Arg
            20                  25                  30

Tyr Thr Asp Leu Asn Tyr Trp Thr Glu Leu Ala Gln Leu Leu Glu Lys
        35                  40                  45

Gly Lys Phe Asp Ala Leu Phe Leu Ala Asp Val Val Gly Ile Tyr Asp
    50                  55                  60

Val Tyr Arg Gln Ser Arg Asp Thr Ala Val Arg Glu Ala Val Gln Ile
65                  70                  75                  80

Pro Val Asn Asp Pro Leu Met Leu Ile Ser Ala Met Ala Tyr Val Thr
                85                  90                  95

Lys His Leu Ala Phe Ala Val Thr Phe Ser Thr Thr Tyr Glu His Pro
            100                 105                 110

Tyr Gly His Ala Arg Arg Met Ser Thr Leu Asp His Leu Thr Lys Gly
        115                 120                 125

Arg Ile Ala Trp Asn Val Val Thr Ser His Leu Pro Ser Ala Asp Lys
    130                 135                 140

Asn Phe Gly Ile Lys Lys Ile Leu Glu His Asp Glu Arg Tyr Asp Leu
145                 150                 155                 160

Ala Asp Glu Tyr Leu Glu Val Cys Tyr Lys Leu Trp Glu Gly Ser Trp
                165                 170                 175

Glu Asp Asn Ala Val Ile Arg Asp Ile Glu Asn Asn Ile Tyr Thr Asp
            180                 185                 190

Pro Ser Lys Val His Glu Ile Asn His Ser Gly Lys Tyr Phe Glu Val
        195                 200                 205

Pro Gly Pro His Leu Cys Glu Pro Ser Pro Gln Arg Thr Pro Val Ile
    210                 215                 220

Tyr Gln Ala Gly Met Ser Glu Arg Gly Arg Glu Phe Ala Ala Lys His
225                 230                 235                 240

Ala Glu Cys Val Phe Leu Gly Gly Lys Asp Val Glu Thr Leu Lys Phe
                245                 250                 255

Phe Val Asp Asp Ile Arg Lys Arg Ala Lys Lys Tyr Gly Arg Asn Pro
            260                 265                 270

Asp His Ile Lys Met Phe Ala Gly Ile Cys Val Ile Val Gly Lys Thr
        275                 280                 285

His Asp Glu Ala Met Glu Lys Leu Asn Ser Phe Gln Lys Tyr Trp Ser
    290                 295                 300

Leu Glu Gly His Leu Ala His Tyr Gly Gly Thr Gly Tyr Asp Leu
305                 310                 315                 320

Ser Lys Tyr Ser Ser Asn Asp Tyr Ile Gly Ser Ile Ser Val Gly Glu
                325                 330                 335

Ile Ile Asn Asn Met Ser Lys Leu Asp Gly Lys Trp Phe Lys Leu Ser
            340                 345                 350
```

Val Gly Thr Pro Lys Lys Val Ala Asp Glu Met Gln Tyr Leu Val Glu
        355                 360                 365

Glu Ala Gly Ile Asp Gly Phe Asn Leu Val Gln Tyr Val Ser Pro Gly
370                 375                 380

Thr Phe Val Asp Phe Ile Glu Leu Val Val Pro Glu Leu Gln Lys Arg
385                 390                 395                 400

Gly Leu Tyr Arg Val Asp Tyr Glu Glu Gly Thr Tyr Arg Glu Lys Leu
                405                 410                 415

Phe Gly Lys Gly Asn Tyr Arg Leu Pro Asp Asp His Ile Ala Ala Arg
            420                 425                 430

Tyr Arg Asn Ile Ser Ser Asn Val
        435                 440

<210> SEQ ID NO 4
<211> LENGTH: 1335
<212> TYPE: DNA
<213> ORGANISM: Geobacillus thermodenitrificans

<400> SEQUENCE: 4
gaattcatga caaaaaaaat ccatattaat gcatttgaaa tgaattgtgt aggtcatata     60
gctcatggac tttggaggca tcctgaaaat cagcggcacc gttatacaga tttgaattat    120
tggacagaac ttgcacaatt attagaaaag gggaaattcg atgctttatt tttagctgat    180
gtagttggaa tttatgatgt ctatagacaa gtagggata ctgcagttcg tgaagctgtt    240
caaattcctg taaatgatcc cttaatgctt atttcagcga tggcctatgt aacaaaacat    300
ctagcattcg ctgtcacctt ctcaacaacc tatgagcatc catatggtca cgcaagacgt    360
atgtcaacat tagatcactt gacaaaaggt agaattgctt ggaatgttgt aacttcgcat    420
ctcccgagtg ctgataagaa ctttggtatc aaaaaaatac ttgaacatga tgagcgttac    480
gatttggcag atgaatatct agaagtgtgt tataaactat gggaagggag ttgggaagat    540
aatgcagtaa ttcgggatat agaaaataat atatatactg atccgagcaa agtacacgaa    600
ataaatcact caggaaaata ttttgaagtt cccggaccac atttatgcga accctctcct    660
cagcgtacgc cagttattta tcaagcaggt atgtccgaac ggggacgcga atttgccgca    720
aaacatgcag aatgtgtttt cttaggtgga aaagatgtag agactctaaa atttttttgtc   780 gacgatataa gaaaaagagc caaaaagtat ggacgtaatc cagatcatat taaaatgttt    840
gccggaatat gtgtaattgt tggaaaaaca catgatgaag caatggaaaa attaaattct    900
ttccaaaaat attggagctt agaaggacat ttagcacatt acggaggtgg aactgggtac    960
gatttatcta aatatagttc taatgattat ataggtagca tatctgtcgg agaaattatt   1020
aataatatga gtaaactcga tggtaaatgg tttaaattat ctgtaggtac tccgaaaaaa   1080
gttgcggacg aaatgcaata tttagttgag gaagcaggta tcgacggatt taatctagta   1140
caatatgtat caccaggtac ttttgttgat tttattgaac tagtagttcc agaattacag   1200
aaacgaggtc tataccgagt agattatgag gaaggaacct atagagaaaa attgttcggt   1260
aaaggaaatt atcgattacc ggatgatcat attgctgcac gatatcgaaa tatttcttca   1320
aatgtataac tcgag                                                    1335

<210> SEQ ID NO 5
<211> LENGTH: 1380
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 5
aagcttataa ctggccgcgg gaaacgtcgg agcatgcatc atcatcatca tcatatgacg    60
aagaagattc atatcaatgc gttcgagatg aattgcgtcg acatattgc gcatgggtta   120 tggcgccatc cagagaatca gcgccatcgc tacacggact tgaattactg gacggaatta   180
gcccagttat tggagaaggg gaagttcgac gcgctattct tggccgacgt cgtcggaatc   240
tacgacgtgt accgccagtc gcgggacacc gccgtgcgcg aggcggtcca gattcctgtc   300
aatgacccat tgatgttgat ttccgcgatg gcctacgtca ccaagcatct agcgttcgcg   360
gtgaccttct ccacgacgta cgaacatcca tacgggcatg cccgacgcat gagcacgtta   420
gaccatttga ccaaggggcg cattgcgtgg aatgtcgtca cctcgcatct accatcggcg   480
gacaagaatt tcgggataaa gaagatattg gagcatgacg aacggtacga cctagccgac   540
gagtacttag aggtctgcta caagttatgg gagggatcgt gggaggacaa tgccgtgata   600
cgggacattg agaataatat ctacaccgac ccaagcaagg tccatgagat caatcattcg   660
ggaaagtact tcgaggtccc tggaccacat ttgtgtgagc cttcgcctca gcgcacccca   720
gtgatctacc aggcggggat gtcggaacga gggcgggagt tcgccgccaa gcatgccgag   780
tgcgtcttct tgggaggcaa ggacgtcgag acgctaaagt tcttcgtcga cgacatacgc   840
aagcgggcga agaagtacgg acgcaatcca gaccatatca agatgttcgc gggcatttgt   900
gtcattgtgg gcaagaccca tgacgaagcg atggaaaagt tgaattcgtt ccagaagtac   960
tggtcgttag agggacatct agcgcattac gggggaggca cggggtacga cttatccaag  1020
tactcgagca atgactacat tgggagcatt tcggtcgggg aaatcatcaa taatatgagc  1080
aagctagacg gaaagtggtt caagctaagc gtcggcacgc caaagaaggt cgcggacgag  1140
atgcagtact tagtcgaaga ggccgggatt gacgggttca atctagtgca atacgtctcc  1200
cctggaacct tcgtcgactt catagagcta gtcgtccctg agttgcagaa gcgcgggtta  1260
taccgcgtcg actacgaaga agggacctac cgcgagaagt tgttcggaaa gggcaattac  1320
cgcttgcctg acgaccatat tgccgcccga taccggaata tctcgtcgaa tgtctaatga  1380

<210> SEQ ID NO 6
<211> LENGTH: 1380
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
aagcttataa ctggccgcgg gaaacgtcgg agcatgcatc atcatcatca tcatatgacg    60
aagaagattc atatcaatgc gttcgagatg aattgcgtcg acatattgc gcatgggtta   120 tggcgccatc cagagaatca gcgccatcgc tacacggact tgaattactg gacggaatta   180
gcccagttat tggagaaggg gaagttcgac gcgctattct tggccgacgt cgtcggaatc   240
tacgacgtgt accgccagtc gcgggacacc gccgtgcgcg aggcggtcca gattcctgtc   300
aatgacccat tgatgttgat ttccgcgatg gcctacgtca ccaagcatct agcgttcgcg   360
gtgaccttct ccacgacgta cgaacatcca tacgggcatg cccgacgcat gagcacgtta   420
gaccatttga ccaaggggcg cattgcgtgg aatgtcgtca cctcgcatct accatcggcg   480
```

```
gacaagaatt tcgggataaa gaagatattg gagcatgacg aacggtacga cctagccgac      540
gagtacttag aggtctgcta caagttatgg gagggatcgt gggaggacaa tgccgtgata      600
cgggacattg agaataatat ctacaccgac ccaagcaagg tccatgagat caatcattcg      660
ggaaagtact tcgaggtccc tggaccacat ttgtgtgagc cttcgcctca gcgcacccca      720
gtgatctacc aggcggggat gtcggaacga gggcgggagt tcgccgccaa gcatgccgag      780
tgcgtcttct tgggaggcaa ggacgtcgag acgctaaagt tcttcgtcga cgacatacgc      840
gagcgggcga aggagtacgg acgcaatcca gaccatatcg acatgttcgc gggcatttgt      900
gtcattgtgg gcaagaccca tgacgaagcg atggaaaagt tgaattcgtt ccagaagtac      960
tggtcgttag agggacatct agcgcattac ggggaggca cggggtacga cttatccaag     1020
tactcgagca atgactacat tgggagcatt tcggtcgggg aaatcatcaa taatatgagc     1080
aagctagacg gaaagtggtt caagctaagc gtcggcacgc caaagaaggt cgcggacgag     1140
atgcagtact tagtcgaaga ggccgggatt gacgggttca atctagtgca atacgtctcc     1200
cctggaacct tcgtcgactt catagagcta gtcgtccctg agttgcagaa gcgcgggtta     1260
taccgcgtcg actacgaaga agggacctac cgcgagaagt tgttcggaaa gggcaattac     1320
cgcttgcctg acgaccatat tgccgcccga taccggaata tctcgtcgaa tgtctaatga     1380

<210> SEQ ID NO 7
<211> LENGTH: 1380
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
aagcttataa ctggccgcgg gaaacgtcgg agcatgcatc atcatcatca tcatatgacg       60
aagaagattc atatcaatgc gttcgagatg aattgcgtcg acatattgc gcatgggtta      120 tggcgccatc cagagaatca gcgccatcgc tacacggact tgaattactg gacggaatta      180
gcccagttat tggagaaggg gaagttcgac gcgctattct tggccgacgt cgtcggaatc      240
tacgacgtgt accgccagtc gcgggacacc gccgtgcgcg aggcggtcca gattcctgtc      300
aatgacccat tgatgttgat ttccgcgatg gcctacgtca ccaagcatct agcgttcgcg      360
gtgaccttct ccacgacgta cgaacatcca tacgggcatg cccgacgcat gagcacgtta      420
gaccatttga ccaaggggcg cattgcgtgg aatgtcgtca cctcgcatct accatcggcg      480
gacaagaatt tcgggataaa gaagatattg gagcatgacg aacggtacga cctagccgac      540
gagtacttag aggtctgcta caagttatgg gagggatcgt gggaggacaa tgccgtgata      600
cgggacattg agaataatat ctacaccgac ccaagcaagg tccatgagat caatcattcg      660
ggaaagtact tcgaggtccc tggaccacat ttgtgtgagc cttcgcctca gcgcacccca      720
gtgatctacc aggcggggat gtcggaacga gggcgggagt tcgccgccaa gcatgccgag      780
tgcgtcttct tgggaggcaa ggacgtcgag acgctaaagt tcttcgtcga cgacatacgc      840
gagcgggcga aggagtacgg acgcaatcca gaccatatcg acatgttcgc gggcatttgt      900
gtcattgtgg gcaagaccca tgacgaagcg atggaaaagt tgaattcgtt ccagaagtac      960
tggtcgttag agggacatct agcgcattac ggggaggca cggggtacga cttatccaag     1020
tactcgagca atgactacat tgggagcatt tcggtcgggg aaatcatcaa taatatgagc     1080
```

```
aagctagacg gaaagtggtt caagctaagc gtcggcacgc cagacgaggt cgcggacgag   1140
atgcagtact tagtcgaaga ggccgggatt gacgggttca atctagtgca atacgtctcc   1200
cctggaacct tcgtcgactt catagagcta gtcgtcctg agttgcagaa gcgcgggtta    1260
taccgcgtcg actacgaaga agggacctac cgcgagaagt tgttcggaaa gggcaattac   1320
cgcttgcctg acgaccatat tgccgcccga taccggaata tctcgtcgaa tgtctaatga   1380
```

<210> SEQ ID NO 8
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Met His His His His His Met Thr Lys Lys Ile His Ile Asn Ala
 1               5                  10                  15

Phe Glu Met Asn Cys Val Gly His Ile Ala His Gly Leu Trp Arg His
                20                  25                  30

Pro Glu Asn Gln Arg His Arg Tyr Thr Asp Leu Asn Tyr Trp Thr Glu
            35                  40                  45

Leu Ala Gln Leu Leu Glu Lys Gly Lys Phe Asp Ala Leu Phe Leu Ala
        50                  55                  60

Asp Val Val Gly Ile Tyr Asp Val Tyr Arg Gln Ser Arg Asp Thr Ala
65                  70                  75                  80

Val Arg Glu Ala Val Gln Ile Pro Val Asn Asp Pro Leu Met Leu Ile
                85                  90                  95

Ser Ala Met Ala Tyr Val Thr Lys His Leu Ala Phe Ala Val Thr Phe
            100                 105                 110

Ser Thr Thr Tyr Glu His Pro Tyr Gly His Ala Arg Arg Met Ser Thr
        115                 120                 125

Leu Asp His Leu Thr Lys Gly Arg Ile Ala Trp Asn Val Val Thr Ser
    130                 135                 140

His Leu Pro Ser Ala Asp Lys Asn Phe Gly Ile Lys Lys Ile Leu Glu
145                 150                 155                 160

His Asp Glu Arg Tyr Asp Leu Ala Asp Glu Tyr Leu Glu Val Cys Tyr
                165                 170                 175

Lys Leu Trp Glu Gly Ser Trp Glu Asp Asn Ala Val Ile Arg Asp Ile
            180                 185                 190

Glu Asn Asn Ile Tyr Thr Asp Pro Ser Lys Val His Glu Ile Asn His
        195                 200                 205

Ser Gly Lys Tyr Phe Glu Val Pro Gly Pro His Leu Cys Glu Pro Ser
    210                 215                 220

Pro Gln Arg Thr Pro Val Ile Tyr Gln Ala Gly Met Ser Glu Arg Gly
225                 230                 235                 240

Arg Glu Phe Ala Ala Lys His Ala Glu Cys Val Phe Leu Gly Gly Lys
                245                 250                 255

Asp Val Glu Thr Leu Lys Phe Phe Val Asp Asp Ile Arg Lys Arg Ala
            260                 265                 270

Lys Lys Tyr Gly Arg Asn Pro Asp His Ile Lys Met Phe Ala Gly Ile
        275                 280                 285

Cys Val Ile Val Gly Lys Thr His Asp Glu Ala Met Glu Lys Leu Asn
    290                 295                 300
```

```
Ser Phe Gln Lys Tyr Trp Ser Leu Glu Gly His Leu Ala His Tyr Gly
305                 310                 315                 320

Gly Gly Thr Gly Tyr Asp Leu Ser Lys Tyr Ser Ser Asn Asp Tyr Ile
                325                 330                 335

Gly Ser Ile Ser Val Gly Glu Ile Ile Asn Asn Met Ser Lys Leu Asp
            340                 345                 350

Gly Lys Trp Phe Lys Leu Ser Val Gly Thr Pro Lys Lys Val Ala Asp
        355                 360                 365

Glu Met Gln Tyr Leu Val Glu Ala Gly Ile Asp Gly Phe Asn Leu
    370                 375                 380

Val Gln Tyr Val Ser Pro Gly Thr Phe Val Asp Phe Ile Glu Leu Val
385                 390                 395                 400

Val Pro Glu Leu Gln Lys Arg Gly Leu Tyr Arg Val Asp Tyr Glu Glu
                405                 410                 415

Gly Thr Tyr Arg Glu Lys Leu Phe Gly Lys Gly Asn Tyr Arg Leu Pro
            420                 425                 430

Asp Asp His Ile Ala Ala Arg Tyr Arg Asn Ile Ser Ser Asn Val
        435                 440                 445
```

<210> SEQ ID NO 9
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Met His His His His His Met Thr Lys Lys Ile His Ile Asn Ala
1               5                   10                  15

Phe Glu Met Asn Cys Val Gly His Ile Ala His Gly Leu Trp Arg His
                20                  25                  30

Pro Glu Asn Gln Arg His Arg Tyr Thr Asp Leu Asn Tyr Trp Thr Glu
            35                  40                  45

Leu Ala Gln Leu Leu Glu Lys Gly Lys Phe Asp Ala Leu Phe Leu Ala
50                  55                  60

Asp Val Val Gly Ile Tyr Asp Val Tyr Arg Gln Ser Arg Asp Thr Ala
65                  70                  75                  80

Val Arg Glu Ala Val Gln Ile Pro Val Asn Asp Pro Leu Met Leu Ile
                85                  90                  95

Ser Ala Met Ala Tyr Val Thr Lys His Leu Ala Phe Ala Val Thr Phe
            100                 105                 110

Ser Thr Thr Tyr Glu His Pro Tyr Gly His Ala Arg Arg Met Ser Thr
        115                 120                 125

Leu Asp His Leu Thr Lys Gly Arg Ile Ala Trp Asn Val Val Thr Ser
130                 135                 140

His Leu Pro Ser Ala Asp Lys Asn Phe Gly Ile Lys Lys Ile Leu Glu
145                 150                 155                 160

His Asp Glu Arg Tyr Asp Leu Ala Asp Glu Tyr Leu Glu Val Cys Tyr
                165                 170                 175

Lys Leu Trp Glu Gly Ser Trp Glu Asp Asn Ala Val Ile Arg Asp Ile
            180                 185                 190

Glu Asn Asn Ile Tyr Thr Asp Pro Ser Lys Val His Glu Ile Asn His
        195                 200                 205

Ser Gly Lys Tyr Phe Glu Val Pro Gly Pro His Leu Cys Glu Pro Ser
```

```
              210                 215                 220
Pro Gln Arg Thr Pro Val Ile Tyr Gln Ala Gly Met Ser Glu Arg Gly
225                 230                 235                 240

Arg Glu Phe Ala Ala Lys His Ala Glu Cys Val Phe Leu Gly Gly Lys
                245                 250                 255

Asp Val Glu Thr Leu Lys Phe Phe Val Asp Asp Ile Arg Glu Arg Ala
                260                 265                 270

Lys Glu Tyr Gly Arg Asn Pro Asp His Ile Asp Met Phe Ala Gly Ile
                275                 280                 285

Cys Val Ile Val Gly Lys Thr His Asp Glu Ala Met Glu Lys Leu Asn
                290                 295                 300

Ser Phe Gln Lys Tyr Trp Ser Leu Glu Gly His Leu Ala His Tyr Gly
305                 310                 315                 320

Gly Gly Thr Gly Tyr Asp Leu Ser Lys Tyr Ser Ser Asn Asp Tyr Ile
                325                 330                 335

Gly Ser Ile Ser Val Gly Glu Ile Ile Asn Asn Met Ser Lys Leu Asp
                340                 345                 350

Gly Lys Trp Phe Lys Leu Ser Val Gly Thr Pro Lys Lys Val Ala Asp
                355                 360                 365

Glu Met Gln Tyr Leu Val Glu Glu Ala Gly Ile Asp Gly Phe Asn Leu
                370                 375                 380

Val Gln Tyr Val Ser Pro Gly Thr Phe Val Asp Phe Ile Glu Leu Val
385                 390                 395                 400

Val Pro Glu Leu Gln Lys Arg Gly Leu Tyr Arg Val Asp Tyr Glu Glu
                405                 410                 415

Gly Thr Tyr Arg Glu Lys Leu Phe Gly Lys Gly Asn Tyr Arg Leu Pro
                420                 425                 430

Asp Asp His Ile Ala Ala Arg Tyr Arg Asn Ile Ser Ser Asn Val
                435                 440                 445

<210> SEQ ID NO 10
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met His His His His His Met Thr Lys Lys Ile His Ile Asn Ala
1               5                   10                  15

Phe Glu Met Asn Cys Val Gly His Ile Ala His Gly Leu Trp Arg His
                20                  25                  30

Pro Glu Asn Gln Arg His Arg Tyr Thr Asp Leu Asn Tyr Trp Thr Glu
                35                  40                  45

Leu Ala Gln Leu Leu Glu Lys Gly Lys Phe Asp Ala Leu Phe Leu Ala
                50                  55                  60

Asp Val Val Gly Ile Tyr Asp Val Tyr Arg Gln Ser Arg Asp Thr Ala
65                  70                  75                  80

Val Arg Glu Ala Val Gln Ile Pro Val Asn Asp Pro Leu Met Leu Ile
                85                  90                  95

Ser Ala Met Ala Tyr Val Thr Lys His Leu Ala Phe Ala Val Thr Phe
                100                 105                 110

Ser Thr Thr Tyr Glu His Pro Tyr Gly His Ala Arg Arg Met Ser Thr
                115                 120                 125
```

Leu Asp His Leu Thr Lys Gly Arg Ile Ala Trp Asn Val Val Thr Ser
130                 135                 140

His Leu Pro Ser Ala Asp Lys Asn Phe Gly Ile Lys Lys Ile Leu Glu
145                 150                 155                 160

His Asp Glu Arg Tyr Asp Leu Ala Asp Glu Tyr Leu Glu Val Cys Tyr
                165                 170                 175

Lys Leu Trp Glu Gly Ser Trp Glu Asp Asn Ala Val Ile Arg Asp Ile
            180                 185                 190

Glu Asn Asn Ile Tyr Thr Asp Pro Ser Lys Val His Glu Ile Asn His
        195                 200                 205

Ser Gly Lys Tyr Phe Glu Val Pro Gly Pro His Leu Cys Glu Pro Ser
210                 215                 220

Pro Gln Arg Thr Pro Val Ile Tyr Gln Ala Gly Met Ser Glu Arg Gly
225                 230                 235                 240

Arg Glu Phe Ala Ala Lys His Ala Glu Cys Val Phe Leu Gly Gly Lys
                245                 250                 255

Asp Val Glu Thr Leu Lys Phe Phe Val Asp Asp Ile Arg Glu Arg Ala
            260                 265                 270

Lys Glu Tyr Gly Arg Asn Pro Asp His Ile Asp Met Phe Ala Gly Ile
        275                 280                 285

Cys Val Ile Val Gly Lys Thr His Asp Glu Ala Met Glu Lys Leu Asn
290                 295                 300

Ser Phe Gln Lys Tyr Trp Ser Leu Glu Gly His Leu Ala His Tyr Gly
305                 310                 315                 320

Gly Gly Thr Gly Tyr Asp Leu Ser Lys Tyr Ser Ser Asn Asp Tyr Ile
                325                 330                 335

Gly Ser Ile Ser Val Gly Glu Ile Ile Asn Asn Met Ser Lys Leu Asp
            340                 345                 350

Gly Lys Trp Phe Lys Leu Ser Val Gly Thr Pro Asp Glu Val Ala Asp
        355                 360                 365

Glu Met Gln Tyr Leu Val Glu Glu Ala Gly Ile Asp Gly Phe Asn Leu
370                 375                 380

Val Gln Tyr Val Ser Pro Gly Thr Phe Val Asp Phe Ile Glu Leu Val
385                 390                 395                 400

Val Pro Glu Leu Gln Lys Arg Gly Leu Tyr Arg Val Asp Tyr Glu Glu
                405                 410                 415

Gly Thr Tyr Arg Glu Lys Leu Phe Gly Lys Gly Asn Tyr Arg Leu Pro
            420                 425                 430

Asp Asp His Ile Ala Ala Arg Tyr Arg Asn Ile Ser Ser Asn Val
        435                 440                 445

<210> SEQ ID NO 11
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 11
ccccgcaagc ttataactgg ccgcgggaaa cgtcggagca tgcatcatca tcatcatcat    60
atgac                                                                65

<210> SEQ ID NO 12

```
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
gcggtggcgg ccgccgcgcc gaaaaatgcg a                                    31

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Met"
<220> FEATURE:
<221> NAME/KEY: misc_feature
<222> LOCATION: (3)..(3)
<223> OTHER INFORMATION: /note="Residue given in the sequence has no
      preference with respect to the annotation for said position"
<220> FEATURE:
<221> NAME/KEY: MOD_RES
<222> LOCATION: (4)..(4)
<223> OTHER INFORMATION: Any amino acid

<400> SEQUENCE: 13

His Glu Leu Xaa His Lys
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(4)
<223> OTHER INFORMATION: Any amino acid

<400> SEQUENCE: 14

Glu His Xaa Xaa Gly His His
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Ala"
<220> FEATURE:
<221> NAME/KEY: misc_feature
<222> LOCATION: (5)..(5)
<223> OTHER INFORMATION: /note="Residue given in the sequence has no
      preference with respect to the annotation for said position"

<400> SEQUENCE: 15
```

```
Leu Gln Arg His Ser Asp His His Ala
1               5

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 16

His His His His His His
1               5
```

MICROBIAL ENHANCED OIL RECOVERY METHODS UTILIZING A MICROORGANISM THAT IS DEFICIENT IN ITS ABILITY TO DEGRADE SHORT CHAIN HYDROCARBONS

CROSS-REFERENCE TO RELATED APPLICATIONS

This application is a continuation of U.S. application Ser. No. 13/656,294, filed Oct. 19, 2012, which is a divisional of U.S. application Ser. No. 12/869,647, filed Aug. 26, 2010, now U.S. Pat. No. 8,316,933, which claims priority under 35 USC Section 119(e) and the benefit of U.S. Provisional Application No. 61/238,044, filed Aug. 28, 2009, the entire disclosures of which are hereby incorporated by reference in their entireties.

FIELD OF THE INVENTION

The present invention is from the field of microbial enhanced oil recovery (MEOR). In particular, the invention concerns new, efficient, economical and environmentally safe microbial methods to enhance oil recovery in existing oil reservoirs, as well as microorganisms useful in such methods.

BACKGROUND OF THE INVENTION

Background

The demand for crude oil has exceeded the existing production in the United States for more than 30 years. This has led to increasing demand for more imported oil and a dependency on foreign suppliers. The growth of emerging economies is rapidly increasing the demand for oil in the global market. It has been estimated that more than half of all conventional oil (oil that can be produced with current technology) has been produced. Most of the remaining conventional oil is located in the Eastern Hemisphere or in environmentally sensitive areas such as the North Pole. The lack of conventional oil supplies could keep oil prices so high that oil dependent nations such as the United States would be unable to fund the development of alternative energy technologies and be forced into dependency on foreign alternative energy as well. Therefore any new technology that could increase the efficiency of oil recovery would be of great benefit to countries such as the U.S. that have large amounts of unrecoverable oil in place (OIP) in older existing oil fields.

Most oil fields are small and are spread out in the 600 or so sediment basins throughout the world. Most of these oil-producing basins have been explored. Generally the largest fields are discovered first, and further exploration finds only smaller reservoirs. Most of the world's petroleum is found in large fields. Only 37 supergiant oil fields of over 5 billion barrels have been found. These 37 fields account for 80% of all the known oil. Only two of these supergiants are in North America and 26 are in the Persian Gulf. Most of the remaining undeveloped oil in the Western Hemisphere is not light petroleum, but is heavy oil or tar sands. Large deposits of heavy oil are in Venezuela and California. Canada has large deposits of tar sands. Currently, production of heavy oil requires large amounts of energy.

Most petroleum is found in sandstone, siltstone or carbonate. Porosities vary from 5% to 30%. The porous rock, covered with an impermeable layer, collects oil from organic matter in lower source rock. It is a process that takes millions of years. The maturation process converts it to a complex mixture of hydrocarbons of about 82 to 87% carbon and 12 to 15% hydrogen. The oil moves into the porous rock in low concentrations with water. To become a reservoir the porous rock must have some type of impermeable cap-rock that traps the oil. Most traps are anticlinal upfolds of strata that are oval shape, however, fault-traps and salt-domes are also common. Oil near the surface often encounters descending meteoric water that brings in oxygen and bacteria that degrade the oil to heavy oil or tar. Oil is usually not found below 4,900 meters because the high temperature of deep rock will degrade the petroleum into natural gas. Therefore, most oil is between 760 m and 4,900 m deep.

Unlike natural gas, the recovery of petroleum oil is not efficient. The existing conventional oil production technologies are able to recover only about one-half of the oil originally in place in a reservoir of light oil. For heavy oil, the recovery is often less than 10%. Tar sands are so heavy that they will not flow at all and no oil can be recovered by conventional drilling and pumping. A technology that could recover a greater percentage of this residual oil could increase oil production from existing reservoirs and reduce the need of the U.S. to imported oil. The additional oil recovered from existing oil producing reservoirs could reduce the need to explore and develop wilderness areas that are potential new oil fields. This additional recovery of existing oil could bridge the gap needed for the development of alternative renewable energy sources.

The Original Oil In Place (OOIP) is the petroleum present in the oil reservoir when first discovered. The volume of the reservoir is determined by the size and porosity of the carbonate or sand stone. The porosity of the rock is a measure of the amount of small chambers or micro-traps within the rock that can hold water or oil. The oil is generally pushed up to the surface with the existing oil reservoir pressures at first. The pressure in the oil well drops with time and there is a need to create overpressure with other means such as water injection or a gas injection for secondary recovery of the OOIP. The choice of a specific secondary recovery technique depends on the type of the hydrocarbon accumulation and the nature of the reservoir. Water injection or "water sweep" or "waterflooding" is a common secondary recovery technique. In waterflooding, pressurized water is injected into the oil-bearing formation rock. Ideally, the injected water displaces the residual oil and moves it to a producing well. Generally in waterflooding, crude oil free of water is recovered first, and then subsequently a mixture of crude oil and water are recovered from the production wells. At some point, the percentage of water in the oil-water mixture (referred to as the water cut) from this technique becomes so high that it is uneconomical to continue pumping oil from the well. The problem, with using water as a "drive fluid", is that water and oil are immiscible. The lower viscosity water will flow over the oil and by-pass large amounts of oil. Therefore, even after secondary recovery, a significant portion of crude oil remains in the formation, in some cases up to 75% of the OOIP. The fraction of unrecoverable crude oil is typically highest for heavy oils, tar, and large complex hydrocarbons. In the U.S. this residual OIP in old oil wells could be as much as 300 billion barrels of light oil. World-wide, the estimate of unrecoverable oil is 2 trillion barrels. There are an additional 5 trillion barrels of heavy oil, most of which is unrecoverable. Much of this remaining oil is in micro-traps due to capillary forces or adsorbed onto mineral surfaces (irreducible oil saturation) as well as bypassed oil within the rock formation.

Enhanced Oil Recovery

Oil recovery by injection of fluids not normally found in the reservoir is referred to as Enhanced Oil Recovery (EOR). It is a subset of Improved Oil Recovery (IOR), which can include operational strategies such as infill drilling and horizontal drilling. Although it is sometimes referred to as tertiary recovery, it can be implemented along with secondary processes. Many types of EOR have been proposed and used over the years. Technical complexity and the high cost of chemicals have prevented the widespread use of EOR to where it only represents about 10% of total United States oil production.

There have been two major EOR approaches; thermal and non-thermal.

Thermal Processes

Thermal processes work by heating the reservoir rock and the oil to reduce viscosity of the heavy oil. In general, the lower the viscosity of the oil, the better its recovery will be. The most widely used thermal process is steam injection in which the temperature of the reservoir and the remaining oil is increased by heat energy of steam. Hot water may also be used, but it is not as efficient at transferring heat to the oil and rock in the reservoir. Unfortunately, in both processes, most of the heat energy is lost to the surroundings and does not go to heating the oil. In situ combustion of the oil is much more efficient than steam because it only heats the reservoir and not all the pipes and overburden rock. However, in situ combustion is difficult to control and is seldom used. Typically, it requires the energy equivalent of a half a barrel of oil to recover a barrel of oil with a steam injected thermal process. However, this depends on the oil saturation and the configuration of the reservoir. Because most of the energy carried by the steam is given up to the pipes, wall rock, and reservoir, it is best to use only on reservoirs with a high oil content so as to recover as much oil as possible with the steam used to heat the reservoir rock. Generally, thermal methods are used on heavy oil because it reduces the viscosity of the oil and increases the mobility of the oil and the mobility ratio (mobility of displacing fluid to mobility of displaced fluid or oil). Typically, recoveries are in the range of 50 to 60% for a thermal process, but the net energy gain is much less than that because of the large amount of energy needed to make steam.

Non-Thermal Processes

Several non-thermal processes have been experimented with or used over the years. These rely on a combination of reducing the oil viscosity and decreasing the interfacial tension (IFT) between the oil and displacing fluid. Ideally, the mobility of the displacing fluid should not be higher than the oil. The mobility ratio (mobility of displacing fluid over mobility of displaced fluid) should be low. The mobility of the oil can be increased by viscosity reduction and by IFT reduction. As the IFT is decreased, the oil becomes more miscible with the fluid until it becomes one phase and the IFT is zero. This decreases the mobility ratio and increases the oil recovery. Alternatively, the viscosity of the displacing fluid can be increased by adding polymers to "thicken" the liquid. Non-thermal methods require less energy and are best suited for light oil of 100 cp or less. However, most non-thermal methods require considerable laboratory experimentation and process optimization.

Microbial Enhanced Oil Recovery (MEOR)

One special type of EOR technique uses microorganisms such as bacteria and archaea to dislodge the micro-trapped or adsorbed oil from the rock. The goal of this technique, which is known as microbial enhanced oil recovery (MEOR), is to increase oil recovery of the original subsurface hydrocarbons using bacteria rather than the more costly chemical recovery processes. These biological processes typically use microorganisms to achieve similar results as the chemical methods in that they reduce IFT and reduce the mobility ratio of the water drive fluid to oil. The major mechanisms that microbes are believed to operate by are they: (1) alter the permeability of the subterranean formation by producing low molecular weight acids from the biodegradation of hydrocarbons which cause rock dissolution, (2) produce biosurfactants that can decrease IFT and form micelles of oil in water, (3) mediate changes in wet-ability of the oil droplet by growing on the droplet and changing the surface of the oil to a less hydrophobic surface (4) produce bio-polymers that improve the mobility ratio of water to petroleum by increasing the viscosity of water and plug high flow channels, (5) produce lower molecular weight hydrocarbons by enzymatically cleaving the large hydrocarbons into smaller molecules, and thereby reduce the oil's viscosity, (6) generate gases (predominantly carbon dioxide and nitrogen) that increase formation pressure.

Of all the EOR processes, MEOR is presently considered the lowest cost approach, but is generally the least often used. The main reason this biological process is not more widely used, is that it is not always successful or predicable. Furthermore, bacteria in oil wells, pipes and tanks are known to cause problems. In fact, it is believed that high viscosity heavy oil such as oil sands are the result of bacteria consuming the lighter weight petroleum components and leaving behind the high molecular weight fractions which are less readily consumed by the bacteria. Therefore many petroleum engineers see bacteria as a problem, not a solution. In fact, if not used correctly, the growth of bacteria could degrade the oil or increase the hydrogen sulfide concentration in the reservoir.

Numerous microorganisms have been proposed for achieving various microbial objectives in subterranean formations. Early MEOR techniques involved injection of an exogenous microbial population into old and low producing oil wells. The inoculating culture was supplied with nutrients and mineral salts as additives to the water pumped into wells for oil recovery. The development of exogenous microorganisms has been limited by the conditions that prevail in the formation. Physical constraints, such as the small and variable formation pore sizes together with the high temperature, salinity and pressure of fluids in the formation and the low concentration of oxygen in the formation waters severely limit the types and number of microorganisms that can be injected and thrive in the formation. Later, it became apparent that indigenous microbes stimulated by the nutrients were playing the major role in oil recovery. Accordingly, many attempts at biological oil recovery do not inject bacteria at all, but rely on indigenous microorganisms exiting in the extreme environment of the oil reservoir.

Biological constraints, such as competition from indigenous microbes and the stress of changing environments (from surface to subsurface) also act to limit the viability of exogenous microorganisms. To overcome these problems, the use of indigenous microorganisms, commonly anaerobic, has been proposed in MEOR projects. It is known that bacteria and other microbes that can grow indigenously within petroleum oil reservoirs and can be used to enhance oil production. It is also known that bacteria and other microbes will metabolize various components of petroleum as a carbon and energy source. In addition to the beneficial effects of making surfactants, solvents and other metabolites that can result in an increase in oil production; they can also consume oil as a carbon source. Unfortunately, they especially prefer to consume the short-length alkanes, not the heavy viscous oil.

In fact, the process of petroleum bio-degradation relies on the emulsification of oil so that the hydrocarbon can be transported into the bacterial cells for conversion to fatty acids as a carbon and energy source. This process can be used to remediate oil spills and other oil contaminated sites by supplying the indigenous microbes with nutrients or inoculating with cultures of microbes that can degrade oil. In the case of biological remediation of petroleum contaminated sites, microbes can produce metabolites such as surfactants that help emulsify oil so that they can then use the emulsified oil as a carbon source. The process of petroleum bio-degradation relies on the emulsification of oil so that the hydrocarbon can be transported into the cell for conversion to fatty acids as a carbon and energy source. Both of these functions help remove the hydrocarbon contamination from the site. However, in the case of MEOR only the production of metabolites such as surfactants, bio-polymers, hydrocarbon cleaving enzymes, organic acids and solvents are beneficial to increased oil production. Other than providing an energy source, the consumption of light petroleum is not beneficial to enhanced oil production from the reservoir.

The biodegradation of the shorter carbon alkane chains reduces the lighter fraction of the hydrocarbon mixture in the petroleum oil. The removal of the short chain alkanes from this mixture increases the overall viscosity of the hydrocarbon mixture. The higher viscosity is more difficult to recover from the reservoir. The percent of recoverable oil is decreased. Also the oil that is recovered is more difficult to transport through pipes and to refine. Therefore the production of useful compounds, by microbes for improved oil recovery, comes with a high cost.

The process of stimulating all the indigenous microbes in an oil reservoir by adding nutrients is therefore unpredictable. The growth of the microbes could produce the beneficial effect of dislodging oil entrapped within a petroleum reservoir. Alternatively, the side effect of light oil consumption could make the oil more viscous and lower the total recovery of oil.

It would be less detrimental if all petroleum components were degraded equally, but the case is that the shorter chain alkanes and lower molecular weight aromatics are more readily degraded by the microbes as a carbon and energy source. This is supported by the fact that petroleum deposits near the surface and most subject to biodegradation are generally very high in high viscosity oil made up of high levels of asphaltic hydrocarbon and fairly low on light (short) chain alkanes. Canadian tar sands are believed to be the heavy residue representing about 10% of the petroleum deposit that has been degraded.

In the past, others have taught ways of augmenting the growth of microbes that dislodge and mobilize oil from underground petroleum reservoirs. These methods generally recommend adding nutrients. Some have also taught adding various cultures of selected bacteria that added beneficial capabilities. Some have even reported isolating microbes that can only degrade higher molecular weight hydrocarbons (U.S. Pat. No. 5,013,654). However, adding these selected cultures is not enough. Although these prior methods disclosed that microbes exist that can only feed on high molecular weight oil, they failed to provide methods of increasing the bio-digestion of heavy oils, while suppressing the lighter weight hydrocarbon consumption by other indigenous microbes. The microbes that were simply residing within the petroleum reservoir are likely to have the ability to degrade lower weight oil. Adding needed nutrients would stimulate the growth of all the microbes present. Because the smaller hydrocarbons can be transported across the cell membrane, the light weight oil consumers will grow faster than the high weight oil consumers and predominate in the population that results from stimulation.

The prior art does not teach methods that prevent the faster biodegradation of the light weight low-viscosity oil in comparison to the slower biodegradation of the higher weight viscous oil. Therefore, the same process that is beneficial to oil recovery is also detrimental to oil viscosity, and it is known that increasing the viscosity of the residual petroleum held within the reservoir will decrease oil recovery. Therefore, prior methods of adding nutrients, either with or without specially selected or engineered microbes, are unpredictable in terms of their ability to increase oil production.

Accordingly, there is a great need for new enhanced oil recovery approaches that are energy efficient, and can be reliably and successfully used in large field situations to enable the recovery of currently unrecoverable oil in existing oil fields.

SUMMARY OF THE INVENTION

It is an object of this invention to provide microorganisms with genes that are useful to enhance recovery of petroleum oil from underground reservoirs, oil sands and other sources of heavy oil while suppressing the consumption of the lighter fraction of the petroleum. In addition, it is an object of this invention to give the host or recipient organism of these genes a competitive advantage for the special environment of the hydrocarbon resource reservoir.

It is another object of the present invention to enable the recovery of oil in existing oil fields or other oil reservoirs where such recovery would otherwise not be commercially feasible.

In one aspect, the present invention concerns a method of enhancing oil recovery comprising introducing into an oil reservoir a microorganism, which is a *halophile* and is deficient in its ability to degrade short chain hydrocarbons of about 12 carbons or less. Preferably, the growth of such microorganism is obligately dependent on high salinity, i.e. it is an obligatory *halophile*.

In one embodiment, the microorganism is of the domain Archaea (hereinafter referred to as archaea) or is a bacterium.

In another embodiment, the microorganism, such as an archaea or a bacterium, is present in a culture of microorganisms or in a consortium, while in another embodiment, it may be able to grow in a salinity of about 50,000 ppm or higher.

In a further embodiment, the microorganism is inhibited in acquiring the ability to grow at salinity below about 50,000 ppm from microorganisms indigenous or contaminating the reservoir.

In yet another embodiment, the microorganism is deficient in its ability to degrade hydrocarbons of about 20 carbons or less.

In a further embodiment, in the microorganism one or more metabolic pathways degrading short chain hydrocarbons of about 12 carbons or less are down regulated or deleted.

In a still further embodiment, the microorganism naturally lacks the ability to degrade short chain hydrocarbons of about 12 carbons or less.

In a different embodiment, the microorganism has the ability to utilize aromatic hydrocarbons.

In another embodiment, the microorganism has the ability to utilize hydrocarbon chains of greater than about 12 carbons, or about 20 hydrocarbons.

In yet another embodiment, the microorganism has the ability to utilize modified hydrocarbons containing sulfur.

In a further embodiment, the microorganism has the ability to utilize modified hydrocarbons containing nitrogen.

In a still further embodiment, the microorganism has the ability to utilize simple carbons from the group comprising; glucose, sucrose, mannose, starch, glycerin, organic acids, and other simple sugars.

In a different embodiment, the microorganism has the ability to produce surfactants.

In another embodiment, the microorganism has the ability to produce extra cellular polymers.

In a further embodiment, the microorganism (i) contains functional genes for the metabolism of high molecular weight hydrocarbons; (ii) lacks functional genes for the transport and/or oxidation of short chain alkanes at the cell membrane; (iii) contains functional gene or genes for the production of surfactants; and (iv) is regulated to express said functional gene(s) and grow in a high salt environment within a reservoir.

In all embodiments, the method may further comprise the step of waterflooding the reservoir with low salinity fluid or a fluid containing a compound toxic to said obligatory halophiles to reduce the concentration of halophilic microbes that have the ability to utilize short chain hydrocarbons of about 12 carbons or less, or 20 carbons or less.

In all embodiments, the method may further comprise the step of injecting a nutrient mixture into the reservoir.

In another aspect, the invention concerns a microorganism that (i) is a *halophile*, and (ii) is deficient in its ability to degrade short chain hydrocarbons of about 12 carbons or less.

In one embodiment, the microorganism is an obligatory helophile.

In another embodiment, the microorganism is an archaeon or a bacterium.

In another aspect, the invention concerns a microorganism of the domain Archaea or bacteria that (i) is an obligatory *halophile*, (ii) is deficient in its ability to degrade short chain hydrocarbons of about 12 carbons or less, and wherein (iii) the growth of said microorganism is obligately dependent of high salinity, wherein in various embodiments, the microorganism naturally has and/or is engineered to have the properties (i)-(iii).

In yet another embodiment, the microorganism is able to grow in a salinity of about 50,000 ppm or higher.

In a further embodiment, the microorganism is inhibited in the ability to acquire the ability to grow at salinity below about 50,000 ppm from microorganisms indigenous in or contaminating an oil reservoir.

In a still further embodiment, the microorganism is deficient in its ability to degrade hydrocarbons of about 20 carbons or less.

In a different embodiment, the microorganism has the ability to utilize aromatic hydrocarbons.

In another embodiment, the microorganism has the ability to utilize hydrocarbon chains of greater than 12 carbons.

In yet another embodiment, the microorganism has the ability to utilize modified hydrocarbons containing sulfur.

In a further embodiment, the microorganism has the ability to utilize modified hydrocarbons containing nitrogen.

In a still further embodiment, the microorganism has the ability to utilize simple carbons from the group comprising; glucose, sucrose, mannose, starch, glycerin, organic acids, and other simple sugars.

In a different embodiment, the microorganism of has the ability to produce surfactants.

In another embodiment, the microorganism has the ability to produce extra cellular polymers.

In another aspect, the invention concerns a culture of consortium comprising a microorganism as hereinabove described. In various embodiments, the culture or consortium may comprise, consist essentially of or consist of a plurality of microorganisms as hereinabove defined. In addition, a consortium may comprise microorganisms of different type (e.g. both bacteria and archaea) and/or having different properties selected from the characteristics described above and/or otherwise disclosed herein.

It is noted that two or more of the various embodiments listed above or otherwise disclosed herein can be used in any combination, and any and all of such combinations are within the scope of the present invention.

Figure 1:
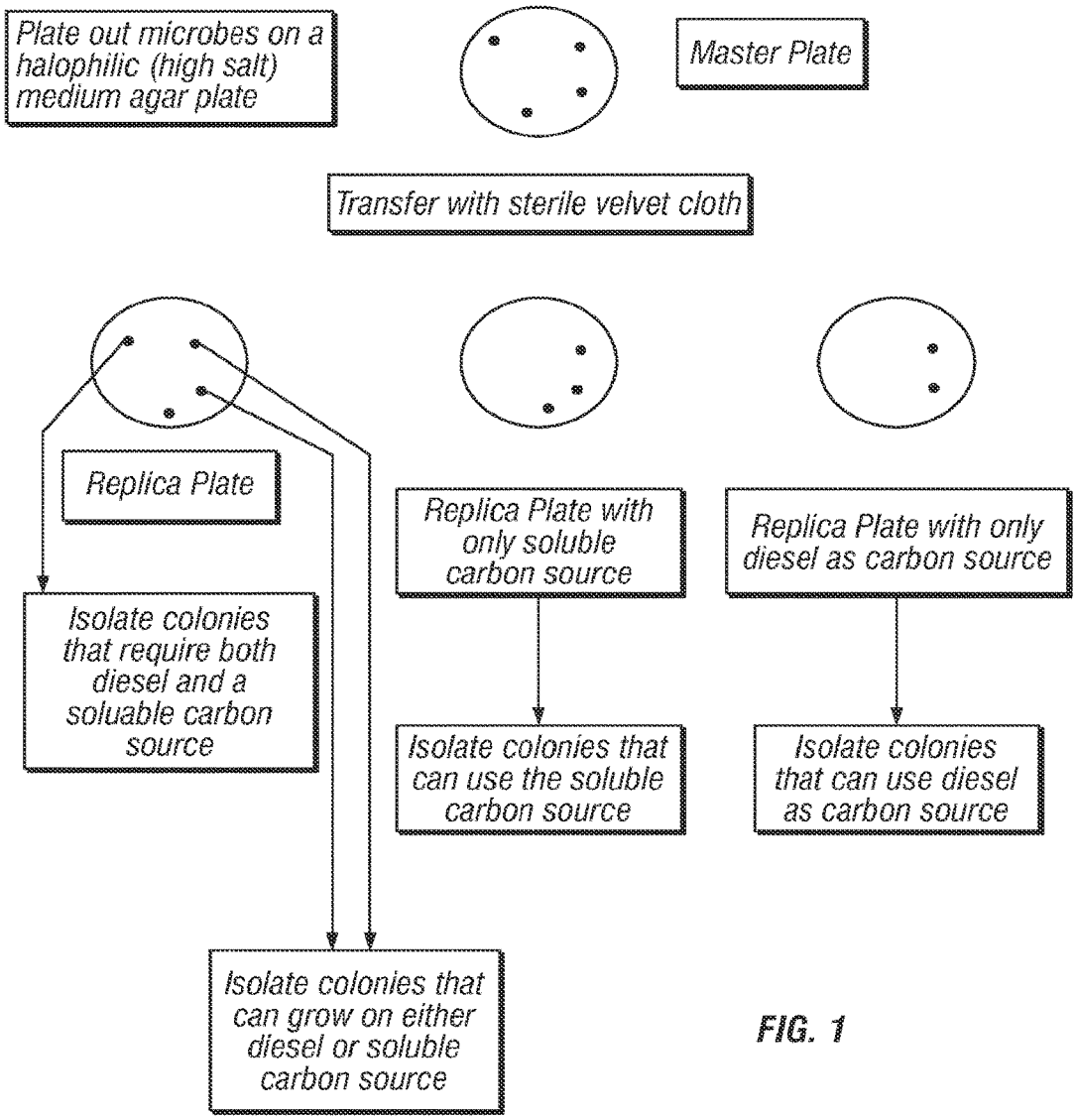
FIG. 1 illustrates a process of replica plating that can be used as part of the present invention.
Figure 2:
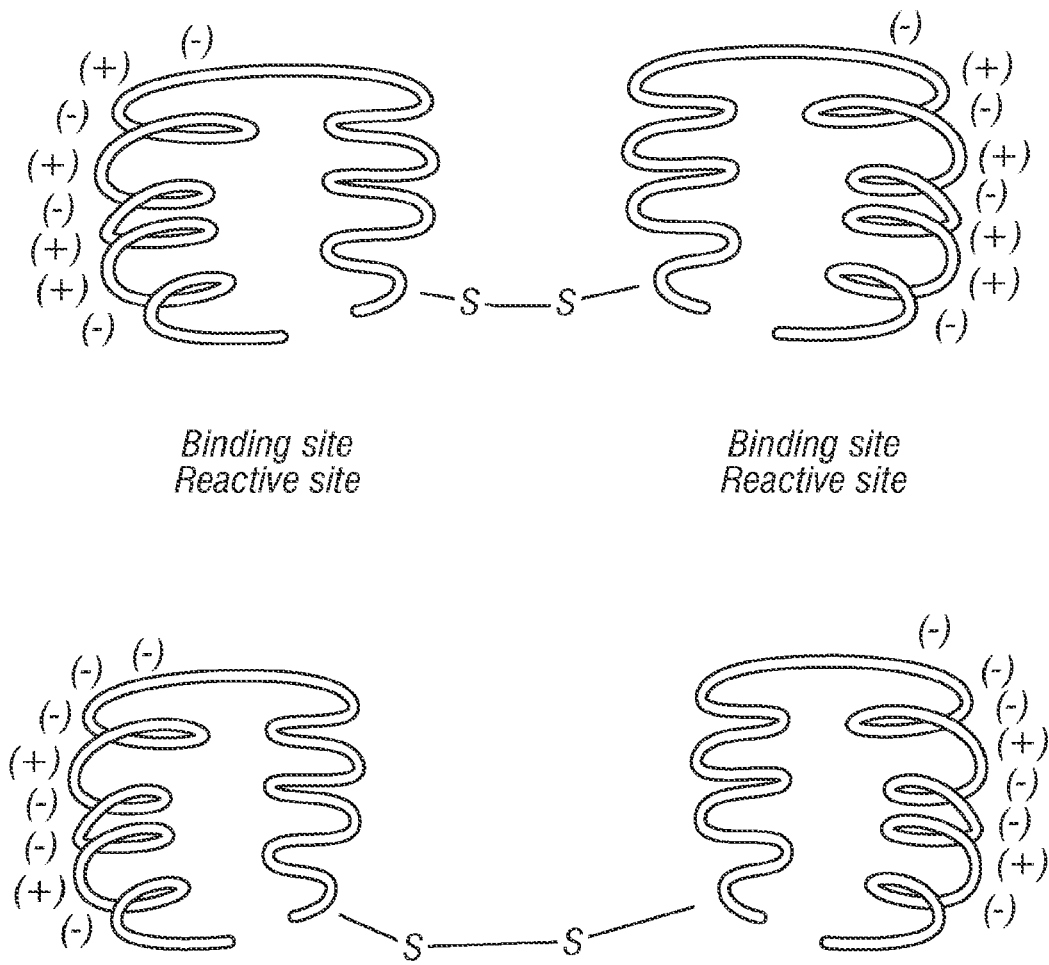
FIG. 2 illustrates the osmotic adaptation of enzymes.

1: GFF40 cell lysate (CL) prior IPTG induction;
2 & 4: GFF40 CL 3 hours post IPTG induction;
3: SeeBlue Plus 2 protein standard;
5: GFF40 CL flow through (FT) Ni-NTA column;
6: 10× volume Ni-NTA column wash solution passed the Column;
7: elute from GFF40 column using elution buffer;
9: elute from GFF31 column
10: elute from HVev [*Haloferax vocanii* (HV) containing an empty vector png168] column
11: elute from HV column.

DETAILED DESCRIPTION OF THE INVENTION

I. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The term "oil reservoir" is used herein in the broadest sense and includes all forms of hydrocarbon deposits, including, without limitation, underground reservoirs, producing wells, non-producing wells, experimental wells, exploratory wells, oil sands and other sources of heavy oil and the like, which may be accessible by any means, such as, for example, one or more wellbores.

The terms "microorganism" and "microbe" are used interchangeably and in the broadest sense, including all types of microorganisms, including bacteria, fungi, archaea, and protists, and microscopic animals, such as plankton, planarian and amoeba. Preferred microbes for the purpose of the present invention are bacteria and archaea.

The term "microbial consortium" is used herein to refer to multiple interacting microbial populations. Members of a consortium communicate with one another. Whether by trading metabolites or by exchanging dedicated molecular signals, each population or individual detects and responds to the presence of others in the consortium. This communication enables a division of labor within the consortium. The overall output of the consortium rests on a combination of tasks performed by constituent individuals or sub-populations.

Archaea comprise one of the three distinct domains of life, with bacteria and eukaryotes. For a review, see, e.g. Makarove and Koonin, *Genome Biology* 4:115 (2003).

The term "*halophile*" is used herein to refer to an extremophile that thrives in environments with very high concentrations, typically at least about 5% (50,000 ppm), or at least about 10%, or at least about 15% of salt.

The term "obligatory *halophile*" is used herein to refer to an extremophile whose growth is obligately dependent on high salt concentrations, typically at least about 5% (50,000 ppm), or at least about 10%, or at least about 15% of salt.

The terms "repression" and "inhibition" with reference to gene expression are used herein interchangeably and refer to any process which results in a decrease in production of a gene product, regardless of the underlying mechanism. A gene product can be either RNA or protein. Gene repression includes processes which decrease transcription of a gene and/or translation of mRNA. Thus, specifically included in this definition are processes that inhibit the formation of a transcription initiation complex along with those that decrease transcription rates and those that antagonize transcriptional activation is gene repression. These repressions can be either reversible or irreversible, both of which are specifically included in this definition.

The term "lateral gene transfer" is used herein in the broadest sense and refers to the transmission of genetic information from one genome to another.

The term "surfactant" as used herein means microbially produced surface-active agents, including, but not limited to, glycolipids (e.g. sophorose lipid or rhamnose lipid), lipoproteins, polysaccharide-fatty acid complexes, mono- and diglycerides, lipoheteropolysaccharides, peptidolipids, neutral lipids, corynomycolic acids, trehalose dimycolates and polysaccharide-protein complexes.

The term "hydrocarbon" is used herein in the broadest sense to describe any organic compound that contains only carbon and hydrogen. The term specifically includes, without limitation, straight and branched chained saturated hydrocarbons (alkanes), straight and branched chained unsaturated hydrocarbons (including alkenes and alkynes), cycloalkanes, and aromatic hydrocarbons (arenes).

A "short chained alkane", as defined herein, contains 1 to 4 carbon atoms.

A "high molecular weight hydrocarbon", as defined herein, is a hydrocarbon having at least about 40 carbons, for example, a hydrocarbon having between about 40 and about 60, or between about 40 and about 80, or between about 40 and about 100, or between about 40 and about 120 carbons.

II. Detailed Description

In the present invention, means are provided to maintain the beneficial aspects of oil mobilizing microbes, while preventing their detrimental effects. One major detrimental effect of microbes is that they can grow in a petroleum reservoir and consume petroleum. Not only do microbes consume petroleum, but they are much faster at consuming the lighter fraction of petroleum oil. The methods provided by this invention are designed to stop or reduce the consumption of beneficial light weight petroleum by the consortium of microbes that is used to make surfactants and other metabolites that are beneficial to enhanced oil production.

According to the present invention, the detrimental effect of light oil consumption is selected out of the consortium. Bacteria and other microbes are carefully selected or modified to be deficient in their ability to consume the lower weight hydrocarbons, especially the shorter chain length (e.g. less than about 20 carbons, or about 12 carbons or less) alkanes. The preferred consortium of microbes is selected, modified or controlled so that the microbial culture relies on either a soluble carbon source provided by the nutrient mixture injected with the microbes and water flood or the bio-consumption of high molecular weight hydrocarbons present in the petroleum. The metabolic pathways that degrade only the higher molecular weight hydrocarbons are not deliberately down regulated or deleted. These pathways are beneficial because not only does the consumption of higher molecular weight carbohydrates provide an additional carbon source, but the removal of high molecular weight oil reduces the viscosity and improves both the value and the recovery of the petroleum.

However, the selection or engineering of a microbial culture that lacks the detrimental effects of consuming light oil is not sufficient. Such a culture could be quickly overcome by indigenous or contaminating microbes that had the ability to consume light weight oil. Even if the engineered culture was robust and quick growing it could acquire genes that coded for the metabolism of light weight oil. This could occur by the process of Lateral Gene Transfer (LGT), which is known to occur in many natural environments. Picking up such genes would give the microbes a competitive or evolutionary advantage and they would soon dominate the population.

This invention provides a means for preventing LGT (also known as horizontal gene transfer) so that the engineered or selected culture of microbes does not acquire unwanted or detrimental pathways for improved oil production. For example, a bacterium that only had genes coding for the enzymes that were required to metabolize polyaromatics, but did not have the genes coding for the enzymes needed for short chain alkane utilization would be good for oil recovery. If it acquired genes from another bacterium that also gave it the ability to metabolize short chain alkanes it would grow faster and would increase in population. This would be a beneficial adaption for the bacteria, but would not benefit the oil recovery process, since it could increase the viscosity of the remaining petroleum mixture Lateral gene transfer is common among bacteria and Archaea as a mechanism of genetic information sharing between different species. It is believed to play a significant role in evolution and is also known to occur in higher organisms. It is somewhat analogous to a computer program being transferred from one computer to another. A gene that codes for specific enzyme can be transferred from a bacterium to yeast in such a way that the yeast could produce the enzyme and obtain that activity. This process can occur in nature as well as in the laboratory.

Some Archaea and bacteria that live in very high salt environments maintain very high salt concentrations inside the cytoplasm. This requires major changes to the surface charges on proteins, enzymes and other cytoplasmic compounds so that they can remain soluble and function in the high salt, low water environment. The process that brought about these changes to "salt in" halophiles, especially obligate halophiles, is believed to have taken thousands, if not millions of years to evolve. Therefore, a gene transferred into a *halophile* from a non-*halophile* or low salt cytoplasmic microbes is unlikely to be functional or produce a functional gene product in a "salt-in" *halophile*. This invention relies on this different high salt "operating system" of obligate halophilic Archaea and bacteria to prevent LGT of short chain utilizing enzymes from non-obligate microbes being acquired by the selected or engineered halophiles for MEOR.

With the ability to prevent the metabolism of light oil, the corresponding viscosity increase, cased by the removal of the light oil fractions, is also prevented. As stated above, the higher the viscosity of oil, the lower the recovery will be. The beneficial effects of the microbes such as reduction of IFT, increase sweep efficiency and improved mobility ratio could be negated by increase in viscosity. However, if the microbes can only consume heavy oil or other carbon sources the major detrimental effect can be avoided. This makes the MEOR process of the present invention more predictable and more effective.

The use of an obligate *halophile* requires that any new genes taken from non-halophiles or low salt-in cytoplasm (non-obligate) halophiles be modified to change the amino acid residue sequences of any proteins they code for. These changes are needed to render the proteins functional and are more soluble at high salt concentrations. These required changes can be determined by analysis of homologues proteins found in both non-halophiles and obligate halophiles. In addition, three dimensional structural analyses can be used to determine surface positively charged resides such as lysine which may be changed to negatively charged amino acid residues such as aspartic acid. This type of amino acid residue changes will result in an increase negative charge, which is generally beneficial to high salt functionality. A large number of potentially beneficial changes can be made and then tested by expression in a model obligate *halophile* such as *Haloferax volcanii*.

The study of hydrocarbon bio-degradation provides an understanding of the mechanism of short chain alkane metabolism. The shorter chain alkanes are made soluble in water generally with the aid of surfactants produced by the bacteria or Archaea. Then the soluble alkane adsorbs onto the cell's hydrophobic membrane and is transported across the membrane of the microbe. Enzymes bound to the membrane convert the alkane to an alcohol. Subsequent chemical reactions catalyzed by other enzymes convert the alcohol to an aldehyde and then to an organic acid also referred to as a fatty acid. The fatty acid can then be further metabolized by the cell for energy and carbon building blocks for its growth. This biology of the short chain alkane metabolism is the most studied and the best understood. Metabolism of larger or higher molecular weight hydrocarbon is more complex and less well understood. The larger or higher weight hydrocarbons are much less soluble and more difficult to transfer across the cell membrane. However, the biodegradation of high molecular weight oil is known to occur, however, it happens at a slower rate. A more detailed description of biological degradation of hydrocarbons is reviewed by J. D. Van Hamme, A. Singh, and O. Ward in *Microbiology and Molecular Biology Reviews*, December 2003, p. 503-549. This invention relies on retarding the light chain alkane metabolism by the engineered or selected microbes.

In the methods of the present invention, genes that code for alkane hydroxylase systems which are capable of degrading light weight and low viscosity hydrocarbons, are inhibited, e.g., deleted, mutated or down regulated in the selected or engineered microbe. In addition, LGT from the environment is prevented. That is, the acquisition of similar genes that code for degradation of light weight oil from other microbes that are present or could contaminate the reservoir is prevented. However, the production of surfactants or other metabolites, beneficial to oil mobilization, is not prevented. The expression of genes needed for the production of surfactants is maintained without the consumption of low viscosity oil.

Different sets of genes code for each of the various metabolic functions that make possible hydrocarbon dependent microbes. The degradation and consumption of the higher molecular weight hydrocarbons is generally enabled by different genes from those in the light chain metabolic pathways. Genes that code for production of important degrading enzymes of hydrocarbon and genes for surfactant production may be regulated by the same promoters, but the gene and gene products are separate and can be manipulated so that they can be independently controlled.

Enzymes that degrade hydrocarbons have different substrate specificities. The first step in the degradation of alkanes is the oxidation of either the terminal carbon or the second to the terminal carbon to form a primary or secondary alcohol. The monooxygenases that catalyze the first step in the metabolism of hydrocarbons have binding sites that show a preference or specificity for different lengths of straight chain alkanes. In addition there are monooxygenases that will oxidize aromatic hydrocarbons of different sizes. Many of the genes have been isolated and their sequences characterized. Many others have not yet been isolated, but are expected to have similar sequences and different specificities. With probes based on highly conserved sequences of key enzymes and variable binding sequence motifs that determine substrate specificity, new genetic information can be obtained from microbes inhabiting petroleum sites.

Currently, there is enough nucleotide and amino acid sequence information available on monooxygenases required for the degradation of various size and types of petroleum hydrocarbons that highly conserved regions have been identified. Some of these highly conserved sequences are required for catalytic activity. Others are substrate specific and will vary with the size and type of hydrocarbon that they oxidize. For example, the 8 histidine amino acid residues that are required for catalytic activity in all alkane monooxygenases are in three histidine boxes (Hist1, HE[L/M]XHK; Hist2, EHXXGHH; and Hist3, LQRH[S/A]DHHA) reported by J. B. van Beilen et al in *Applied and Environmental Microbiology*, December 2002, p. 5933-5942. This knowledge can be used to search for microbes within an environment that can degrade various hydrocarbons. Probes to the highly conserved sites can be used isolate genes that code for monooxygenases that exist within the microbes inhabiting petroleum rich sites. Further analysis based on sequences of the substrate specific sites can identify genes that code for higher molecular weight hydrocarbon utilization.

Although slower than light chain utilization, degradation of heavy chain hydrocarbons can provide a supplemental carbon source without detriment to the value of the petroleum oil. Microbes have been isolated that can only grow on heavy petroleum components. These have been shown to have genes that code for enzymes that are specific for certain of the heavier hydrocarbons and lack the genes for utilization of the lighter short chain alkanes. For example, L. Wang et al reported isolating *Geobacillus thermodenitrificans* NG80-2 from a deep subterranean oil reservoir in northern China that degrades and metabolizes only long chain (C15-C36) n-alkanes, but not short-chain (C8-C14) n-alkanes. The complete genome sequence of *G. thermodenitrificans* NG80-2 has been deposited in the GenBank database (NC_009328 and NC_009329, GenBank CP000557) and is incorporated in the corresponding publication in *Proc Natl Acad Sci USA*, Mar. 27, 2007 p. 5602-5607 by reference. Comparison of gene coding for protein sequences can be used to find specific substrate sequences to make probes for either short or long chain alkane monooxygenases to screen DNA isolated from a specific site or oil reservoir. By this method and other methods of microbiology, the microbes responsible degradation of heavy and light oil in a reservoir can be identified.

In addition to high molecular weight hydrocarbons, petroleum oil contains compounds that are not desirable to have in oil that will be refined into various petroleum products. One major group of undesirable compounds is modified hydrocarbons high in sulfur. Sulfur can be the third most abundant element in crude oil and is especially high in heavy oil. Lowering the sulfur content would increase the value of the crude oil. Bacteria that are capable of selectively attacking the C—S bonds have been isolated and their metabolic pathways elucidated. Most strains studied have been aerobically grown and include; *Rhodococcus erythropolis, Nocardia* spp., *Agrobacterium* sp. Strain MC501, *Mycobacterium* spp., *Gordona* sp. Strain CYKS1, *Klebsiella* spp., *Xanthonmonas* spp., and the thermophile *Paenibacillus*. These bacteria have been shown effective at desulfurization of various sulfur containing hydrocarbons found in crude oil. However, the process is a two phase oil and water system that requires surfactants and energy-intensive mixing. To achieve sulfur removal rate of over 50% high water to oil ratios were needed in well mixed and aerated reactors. The critical aspects of the process include reactor design, product recovery and oil-water separation.

Another group of undesirable hydrocarbons are nitrogenous compounds. Crude oil can contain about 0.5% to 2.1% nitrogen with 70% or more as pyrroles, indoles and carbazole nonbasic compounds. These compounds are poisons to cracking catalysts, toxic and result in air pollution. Removal of the nitrogenous compounds would increase the value of oil recovered by the MEOR process. Several species of bacteria have been isolated that contain metabolic pathways for the oxidative transformation of nitrogenous compounds found in crude oil. A review of these bacterial processes was published by Kaiser, J. P. et al in *Microbiol. Rev.* 60:483-498. The genes responsible for carbazole degradation by *Pseudomonas* sp. strain CA10 were identified and cloned into *E. coli* by Sato et al and were reported to transform a wide range of aromatic compounds. The results are published in *J. Bacteriol.* 179: 4841-4849 in 1997.

Following modification of genes coding for these desulfurization pathways or denitrogenation pathways to be functional and produce functional proteins in the high salt cytoplasm of the host *halophile*, their incorporation into a culture designed for oil recovery can also reduce the sulfur or the nitrogen content of the recovered oil. However, because these are oxidative processes it is important that genes responsible for light chain metabolism be eliminated so that the short chain alkanes are not degraded.

The soluble carbon sources comprise simple sugars, glycerin, starch, fatty acids and other organic molecules that can be metabolized by the consortium of microbes without relying on the same metabolic pathways encoded by genes for the metabolism of alkanes of about 20 carbons or less, such as about 12 carbons or less. If the host or recipient microbe, engineered for the oil reservoir environment, does not contain adequate pathways for the utilization of inexpensive soluble carbon sources, genes required for those pathways could be transferred into the host microbe. Given the opportunity to use a simple carbon source, hydrocarbon degrading microbes will often down regulate the gene clusters containing both the genes for alkane moonooxygenases, and the genes for surfactants that aid in the uptake of hydrocarbons.

That is, by providing a soluble carbon and energy source at sufficient levels to maintain living cells and cell growth, the indigenous microbes may become nondependent on alkane hydrocarbon metabolism for growth and survival. This could lead to down-regulation and low expression of genes or even loss of the genes that code for enzymes that make useful metabolites such as surfactants that emulsify the insoluble hydrocarbons.

Therefore, a means for maintaining high expression and levels of certain genes must be provided. This can be done by number of molecular biology techniques, including, but not limited to, placing the genes coding for each of the metabolic products such as surfactant production under the control of an inducible or constitutive promoter. This will allow for high expression by both transcription and translation of these genes. This is capable of preventing a down regulation that can occur with the wild type promoter when the cell detects a high level of easier to metabolize or preferred carbon source. In conventional MEOR processes that use only naturally occurring cultures of oil consuming microbes in combination with indigenous microbes present in the oil reservoir, the addition of too much of a simple carbon source, such as molasses, could lead to a reduction of surfactant production and unexpectedly lower oil emulsification.

The problem with relying on naturally occurring microbial processes is that they become less effective at both oil degrading and oil recovery when they are supplied with an easily metabolized carbon and energy source, such as molasses. However, not supplying any simple carbon source could slow growth and also lead to low oil production. In addition, the lack of a supplied carbon source will select for the strains of microbes that can utilize the hydrocarbons that exist within the oil reservoir. Furthermore, microbes that have genes that enable them to consume light weight oil will grow and multiply faster than any microbe, added or indigenous, that only contains genes for heavy oil consumption. Therefore, it is best to provide adequate carbon sources for the engineered or selected strains so that they can grow fast enough to prevail over the indigenous strains that have the ability to metabolize short chain alkanes.

Gene promoters contain specific DNA sequences and response elements that are recognized by proteins known as transcription factors. These factors bind to the promoter sequences recruiting RNA polymerase, the enzyme that copies or transcribes the gene coded for in the DNA into a messenger RNA (mRNA). The mRNA can then migrate to a ribosome where it is translated into a protein or gene product. The protein may be a product itself or it may be an important part of the metabolic pathway that is being controlled.

Gene repression and inhibition of expression refer to any process which results in a decrease in production of a gene product, whether by a reversible or an irreversible process. A gene product can be either RNA or protein. Gene repression includes processes which decrease transcription of a gene and/or translation of mRNA. For example, a process that inhibits the formation of a transcription initiation complex or those that decrease transcription rates or those that antagonize transcriptional activation is gene repression.

An inducible promoter is one that is controlled or regulated by some extracellular factor that can increase or decrease the transcription and translation of genes into their products. In a specific example of n-alkane degradation, the alk genes of *Pseudomonas oleovorans* are responsible for the degradation of n-alkanes. These genes are located in two gene clusters that are controlled by a promoter which is controlled by the AlkS protein. This protein is responsive to the hydrocarbon octane. The presence of octane will increase or activate the expression of these genes and their protein products. However, this same promoter is also down regulated or repressed by the presence of a preferred carbon source such as organic acids. These bacteria would both emulsify and degrade n-alkanes unless high levels of a preferred carbon source are supplied. In this case, the genes for hydrocarbon degradation would be turned off. This would limit its usefulness to remediating hydrocarbon contaminated sites and could become less effective if given more easily metabolized carbon sources. However, by inactivating the down regulation of the promoter by preferred carbon sources, and inactivation of genes from the cluster that are needed for the metabolism of alkanes, this microbe can be engineered into an oil emulsifying bacterium that can grow on soluble carbon sources.

One means for inactivating the down regulation by the simple soluble carbon source is to mutate the sequence of the AlkS protein that binds the carbon source in such a way as to not affect the octane binding site. Another method is to transfer the genes coding for the surfactant or bio-polymer production pathway to be under the control of different promoter. This provides a way of controlling the production of surfactant or bio-polymer independent of carbon source.

By maintaining growth on a medium containing a soluble carbon source, the genes that code for short chain alkane hydrocarbon metabolism can by inactivated by a number of means. Methods suitable for inactivation of these genes include, but are not limited to, chemical mutagens and UV and other forms of radiation. In addition, functional genes can be replaced by nonfunctional genes. The technology of gene silencer, developed by A. Fire et al., *Nature* 391(6669): 806-11 (1998), has lead to a better understanding of how genes regulate mammalian cell function. These methods of inactivating specific genes can be used to locate key genes responsible for any metabolic process that a cell or microbe can carry out. In addition, if selected microbes for improved oil do not have completed genomic sequences available in the public domain, the entire genome can be sequenced rapidly by current technology at a fairly low cost.

One functional gene may be used to replace another functional gene. The new gene may also include a reporter gene for easy selection of microbes containing the new gene. For example, a functional cluster of genes that code for a high molecular weight hydrocarbon metabolism pathway may be inserted into a host cell. It may replace a gene cluster for lower molecular weight hydrocarbon metabolism pathway that has been remover or inactivated. In addition, the cell may be given a resistance gene for an antibiotic or other toxin. This is a commonly used method for selecting cells that have successfully incorporated new genetic material. The selected cells can then be grown to large numbers various large scale fermentation techniques known to those skilled in the art biotechnology.

However, there is a potential problem with removing the short chain alkane metabolism genes. The genes that encode for the metabolism of light chain hydrocarbons maybe in clusters with the genes that are required for the production of useful metabolites such as surfactants for the emulsification of oil. Because surfactants are secreted to help the transfer of short chain alkane across the cell membrane they may be combined with the alkane metabolizing genes or controlled by the same promoter. In that case the up regulation of useful metabolites and the down regulation of light chain metabolism may require more complex gene manipulation. That is, key enzymes for the metabolism of short chain alkane should be inactivated not the entire gene cluster related to alkane consumption.

One problem that can prevent the success of this approach is that the genes that code for hydrocarbon emulsification of oil, which helps oil recovery, add no benefit to the microbe if the oil is not being consumed by the bacteria. Also if the bacterial culture has a preferred carbon source in the waterflood fluid, the genes for surfactant production would quickly be lost. A microbial population will generally only carry those genes that are necessary for it to prosper in an environment. If these genes are not needed, they are soon lost. This is why the nutrients, and especially the carbon source, must be carefully controlled if the process only depends upon wild type microbes to either clean up oil spills or recover oil from old wells. Therefore some advantage must be given the engineered microbes to make them better able to survive in the oil reservoir environment. The engineered microbes that can only metabolize high molecular weight oil or produce oil emulsifying surfactants must have a competitive advantage over indigenous microbes that can metabolize short chain alkanes.

It is the object of this invention to provide microbes with genes that are useful for the enhanced recovery of petroleum oil from underground reservoirs, oil sands and other sources of heavy oil while suppressing the consumption of the lighter fraction of the petroleum. In addition, it is the object of this invention to give the host or recipient organism of these genes a competitive advantage for the special environment of the hydrocarbon resource reservoir. By means known to those skilled in the art of molecular biology, genes that are isolated from bacteria and *Achaea* that are indigenous to oil reservoirs or naturally occurring oil seeps that provide beneficial mechanisms for enhanced oil recovery are transfused and expressed at high levels in host microbes. The host microbes are chosen for their survival in the extreme environment of an oil reservoir. The host microbes are provided with a selective advantage for the reservoir environment. In the present invention and in a specific case the selective advantage is high salt concentration tolerance. In addition the engineered or modified microbes could have the ability to utilize a special energy and or carbon source that is supplied in the waterflood fluid. Genes that code for consumption of heavy oil or toxic petroleum components would also be beneficial to both the microbe and oil recovery process. These beneficial genes would be preserved or transferred into the constructed microbes.

This technology is implemented by inoculating an oil reservoir with a culture of one or more microbes each containing combinations of genes for the various mechanisms that are beneficial for improved oil production. The methods of the present invention allow for a wide variety of designs, and thus a combination of mechanisms may be designed for a particular type of reservoir. In addition, a means for controlling and maintaining high expression of these genes may be provided. In certain embodiments, along with the microbes, the present invention also provides the chemical component to create the right environment for the microbes that also suppresses the indigenous microbes that might consume the mobilized oil, especially the short chain alkanes. In this example, a high salt requiring culture of microbes, are inoculated in a salt water fluid supplied to the oil reservoir. This increases the level of salt in the reservoir so as to be toxic to the indigenous microbes, but is preferred for the culture of inoculating engineered or selected microbes. In that case, the indigenous organisms, which might consume light weight oil or produce hydrogen sulfide, will be inhibited or killed. Therefore, the added nutrients will benefit only the growth of the processed-designed microbes and not the growth of detrimental indigenous microbes.

(1) Isolation and Selection of Oil Recovery Genes that Code for Proteins and Pathways for MEOR Over 100 oil degrading microbes have been isolated and reported. Many have been well studied and the sequences of genes related to various functions of the petroleum oil degradation process published. In some cases, for example *Alcanivorax borkumensis* SK2, the complete genome of 3,120,143 base pairs (bp) has been sequenced and published (Schneiker S et al., "Genome sequence of the ubiquitous hydrocarbon-degrading marine bacterium *Alcanivorax borkumensis*.", *Nat Biotechnol*, 2006 August; 24(8):997-1004) and is available from the NCBI Genome Project Database (NC_008260; GenBank AM286690). *A. borkumensis* SK2 is a marine bacterium that uses oil hydrocarbon as its exclusive source of carbon and energy. It grows on predominantly alkanes and often becomes the dominant microbe that may comprise 80% of the microbial community in an oil contaminated environment. Bacteria of the *Alcanivorax* genus belong to a larger group of hydrocarbonoclastic bacteria that also includes the genera of *Cyclolasticus, Marinobacter, Neptunomonas, Oleiphilus, Oleisprira* and *Thalassolituus*. These bacteria are able to metabolize both aliphatic and aromatic hydrocarbons. These bacteria represent a good source of genes that are involved in hydrocarbon utilization pathways.

With the advent of rapid and inexpensive genome sequencing, the bacteria's genes and their roles in hydrocarbon degradation, surfactant production and gene regulation are becoming available. Databases such as GenBank, Swiss Prot, and others provide extensive genomic sequence data from these hydrocarbon degrading microbes. This data can be searched with computer programs such as BLASTX and BLASTN at the National Center for Biotechnology Information. In addition, the use of PCR amplification based on probes with complementary sequences from the highly conserved sequences for enzymes, known to be needed for hydrocarbon degradation, can be used to isolate and characterize homologues genes from new microbes from oil contaminated sites and oil reservoirs. This can be done to analyze the change in protein sequence that has evolved to adapt to different environments. Such methods would be a useful way to find enzyme sequence modification that evolved as adaptation to the specific environmental. For example, microbes isolated from a high salt oil reservoir could contain enzymes that could degrade hydrocarbons in a high saline environment. These enzyme sequences could be compared to homologues enzymes that function in a low salt environment to understand how to modify the sequence of proteins to be soluble and functional in an obligate *halophile*.

In the case of *A. borkumensis* SK2, various gene clusters have been identified that are required for; the degradation of short chain alkanes; the degradation of large alkanes up to 32 carbons in length; and the degradation of branched aliphatic and alkylcycloalkanes. Part of this process of hydrocarbon metabolism is the production of surfactants for the emulsification of various types of hydrocarbons. In the case of the smaller or lower molecular weight chain hydrocarbons, the emulsification aids in the transfer of the hydrocarbon across the cell membrane so that it can be metabolized. Therefore, this gene cluster includes genes useful for mobilization of oil which could be transferred to a host microbe. It also contains genes that are not wanted, such as genes that code for the proteins that are needed for the transfer of small alkanes into the cell for further breakdown and consumption. According to the present invention, the unwanted genes are not transferred to a host microbe or are inactivated or repressed. Genes required for the metabolism of larger alkanes, or alkylcycloalkanes, or polycyclic aromatic hydrocarbons would be candidates for transfer into host microbes.

The lack of enzymes that oxidize short chain alkanes would block or at least slow down the transfer of small alkanes across the membrane. If an obligate *halophile* is engineered to serve as the basis for this invention it can be given the genes that are required for degradation of all the petroleum components that would be beneficial to remove from the produced oil. To compensate for the slower metabolism of these larger and more recalcitrant hydrocarbons, the host *halophile* may also need a soluble carbon and energy source to maintain growth.

Many of the well studied oil degrading microbes are considered to be a useful source of genes sequences required for proteins and pathways to make useful products for the mobilization of petroleum oil. In one example, one or more bio-surfactants may be secreted by the cells to aid in the emulsification of the oil droplets so that the oil can be absorbed through the cell wall. Several strains of *Bacillus subtilis* and *Bacillus licheniformis* have been used to produce a lipopeptide named surfactin at commercial scale. This lipopeptide is also useful as an emulsifier and an antibiotic. Bacteria can be used to produce these surfactants in fermentation with manipulation of environmental and nutritional factors to increase yield as described by Cooper et al. in 1981, *Appl. Environ. Microbiol.* 42:408-412, by Javaheri et al. in 1985, *Appl. Environ. Microbiol.* 50:698-700, and Guerra-Santos et al. in 1986 *Appl. Microbial. Biotech.* 24:443-448. More recently, Mulligan et al. reported in U.S. Pat. No. 5,037,758 a genetically modified strain of *B. subtilis* ATCC #21332 with a mutation at a site in a gene of wild type *B. subtilis* that is able to produce surfactin at much higher concentrations than the wild type. Therefore, by using gene transfer techniques these well studied genes, encoding for surfactant production, can be transferred into various host cells and the production of surfactant controlled.

There are many types of bio-surfactants that are useful in the emulsification of oil. *Pseudomonas aeruginosa* and other species can produce rhamnolipids, which have a different structure than surfactin, but still function to immobilize oil. Other surfactants, such as sophorolipid and mannosylerythritol lipid and glycolipids are produced by various strains of *Candida*. Over 200 different variations of bio-surfactants have been reported. The different surfactant structures have varying degrees of effectiveness depending on the pH, salt concentration and other environmental factors. Because both the sequence and amino acids will affect the solubility of the seven amino acid peptide of the lipopeptide surfactant there are many millions of possible combinations. It is therefore likely that new strains of bacteria with unknown genes controlling the production of different bio-surfactants that are better at mobilizing oil for some reservoir environments could be isolated.

Surfactants and bio-polymers that are functional at high salt concentrations and that are synthesized by either Archaea or bacteria that are adapted to high salt cytoplasm are particularly preferred. The isolation of microbes from environments extremely high in salinity are useful because they may contain genes that code for surfactants and biopolymers that would be useful in the selection and engineering of halophilic microbes for MEOR processes. Recently, Kebbouche-Gana et al. in *J. Ind. Microbiol Biotechnol* (2009) 36:727-738 reported isolating five halophilic Archaea that are able to produce surfactants above 15% salts and that are able to metabolize both simple carbon sources and also diesel. The five halophiles isolated by Kebbouche-Gana et al. are examples of microbe that are likely to have genes containing sequence information regarding enzymes that have adapted to high salt concentrations. A technique for surfactant quantification and screening for biosurfactant-producing microorganisms is given by Bodour A A and Maier R M in *J. Microbiol. Methods* (1998) 32:273-280 and is incorporated by reference. Halophilic Archaea such as *Haloferax medierranei* have been reported to produce extracellular polysaccharides by Anton J. et al in *Appl. Envirn. Microbiol.* (1988) 54:2381-2386. In addition, halotolerant and thermotolerant bacteria have been reported to produce salt and thermo resistant bio-polymers in *Appl. Envirn. Microbiol* (1986) 51:1224-1229 by Pfiffner, S. M. et al. These isolated microbes are possible sources of genes, that with some degree of modification could be transferred into a *halophile* that could be used as part of a culture designed for high salinity MEOR processes. In addition, similar isolation techniques could be used to isolate halophilic Archaea and bacteria from high salinity oil reservoirs that could provide both microbes and genetic information that would be useful in selecting and engineering a culture of microbes for high salinity applications of MEOR.

The process of identifying new genes based on DNA sequence similarity or homology to known gene sequences of similar function is well known to those skilled in the art of molecular biology. Several methods have been used in the past. One method is to make probes of complementary RNA sequence with florescent or radio-labeled tags that will bind to mRNA of the genes being expressed by the bacteria in the environment. A second technique is to use PCR amplification of DNA isolated from the environment with probes made from conserved sequence regions of the sought after genes. A third method used for screening for bioactivities is taught by J. M. Short in U.S. Pat. No. 6,030,779. With any of these methods, new gene sequences can be isolated from environments of interest such as an oil reservoir that is currently undergoing a successful MEOR operation. An alternative is an extreme environment similar to one that might be encountered in an oil reservoir such as high salt concentration. For example, genes that code for a bio-surfactant that is particularly well evolved for high temperature may be isolated from microbes in a high temperature oil reservoir. These genes may then be transferred into a halophilic microbe that could use a soluble carbon source and express a surfactant to immobilize oil in a reservoir that is both high in temperature and also high in salinity.

Another group of oil degrading microbes that are a good source of genes coding for useful products are microbes that can only metabolize higher molecular weight or complex hydrocarbons. For example, Banerjee et al. in U.S. Pat. No. 5,013,654 (1991) reported strains of an aerobic bacterium that will grow on paraffins of chain length longer than 12 carbons. They also isolated a mutant strain of *P. aeruginosa* SB-1, designated SB-3, which has the property of growing on solid paraffins in crude oil of 20 carbons or more, but will not grow on the liquid lighter chain hydrocarbons. Bacteria such as SB-3, which was deposited in the American Type Culture Collection, Washington D.C. as *P. aeruginosa* A.T.C.C. 39615 contain the genes for extracellular degradation and metabolism of heavy petroleum oil. These genes, and others isolated by similar means, can be transferred into a host microorganism that is able to thrive in the extreme environment of an oil well. This ability, combined with the ability to produce various surfactants and biopolymers, and without the ability to consume light oil is useful in recovery of light weight petroleum. If such microorganisms could also use a simple carbon source they could grow fast and predominate the micro-flora of a reservoir. In addition the engineered microbe could be given a toxin resistance gene in addition to salt or temperature tolerance as a further competitive advantage over the indigenous microbes that could consume the light weight oil.

More recently, Lei Wang et al. (PNAS Mar. 27, 2007, vol. 104 (13):5602-7) reported the genomic sequence of a thermophilic *Geobacillus* isolated from a deep oil reservoir that could grow on long chain alkanes up to C36, but was unable to grow on short chain alkanes. Their analysis of the genomic sequence showed that it did not contain any homologous gene sequences to the AlkB genes that code for the membrane bound monooxygenases that oxidize short chain alkanes. This group also reported a soluble and extracellular enzyme for the oxidation of long chain alkanes. This is another example of a source of genes that can be incorporated into a microbe for an additional source of energy and carbon without the detriment of consumption of light weight oil. Microorganisms isolated from heavy oil reservoirs or other oil contaminated locations are likely to contain genes for all types of hydrocarbon metabolizing pathways. The membrane bound monooxygenases evolved in the transport and oxidation of light chain alkanes can be differentiated from extracellular enzymes required for the oxidation of higher molecular weight hydrocarbons which are too large and insoluble to transport across the cell membrane.

In addition to degradation of high molecular weight paraffins, microbes may be able to degrade other unwanted hydrocarbons in petroleum oil. Polycyclic aromatic sulfur containing hydrocarbons such as thiophenes and dibenzothiophenes (DBT) can be present in petroleum at high enough levels that they are toxic to bacteria and detrimental to the refining process. The presence of sulfur compounds in oil will reduce the value of the recovered oil. The sulfur is generally removed prior to refining by expensive chemical processes. The need for a lower cost process has encouraged the development of biological processes based on several species of bacteria that have been isolated that can degrade these sulfur compounds.

In one example, *Rhodococcus* sp. Strain IGTS8 converts DBT to 2-hydroxybiphenyl (HBP) and inorganic sulfur. The pathway requires two monooxygenases and a desulfinase. In addition to sequence characterization, these enzymes have been improved by site directed mutagenesis to broaden the substrate specificity to include thiophenes and benzothiophenes. A more detailed description of the pathway is given by Gray, K. A. et al in *Nature Biotechnology* 14; 1705-1709 (1996). Although this biodesulfurization of crude oil is efficient at removing sulfur with little reduction in fuel value its wide spread use has been inhibited by the cost of operating large stirred and aerated reactors. The reactor cost problem can be eliminated by transferring the genes that code for the proteins in the metabolic pathway into a host *halophile* in such a way that they function in an oil reservoir to degrade the sulfur containing hydrocarbons at the same time as oil is being released from the reservoir during waterflood MEOR.

In summary, the preferred microbe of the present invention (i) contains functional genes for the metabolism of high molecular weight or the less desirable hydrocarbons; (ii) lacks functional genes for the transport and oxidation of short chain alkanes at the cell membrane; (iii) contains the genes for the production of useful compounds for oil recovery and mobilization such as surfactants and polymers; and (iv) is regulated to express the useful compounds at high levels even if given a simple carbon nutrient supplement. In a preferred embodiment, the microbe is capable of functioning and growing in the extreme high salt environment of a petroleum reservoir. In another preferred embodiment, the microorganism is capable of functioning in either an aerobic or a limited oxygen environment. With prevention of short chain alkane degradation the interdiction of air containing oxygen is able to speed growth and oxidative degradation of large high molecular weight hydrocarbons into smaller light weight hydrocarbons for the reduction of oil viscosity. In addition the petroleum's content of sulfur and nitrogen can be reduced, if desired.

(2) Selection of Extremophiles

Microorganisms that thrive in environments that would kill most organisms are referred to as extremophiles. These environments may contain organisms from all three domains although generally are almost exclusively populated by prokaryotes, many which belong to the Archaea domain of organisms. One type of extreme environment is a hypersaline environment. Naturally occurring aquatics of extremely high salt concentration have existed on the earth many million years. Current examples are salt lakes or the Dead Sea as well as some petroleum reservoirs, all of which have existed for many years at salt concentrations several times higher than sea water. This has allowed the evolution of organisms that have adapted to these consistently high salt concentrations. The same is true for high temperature aquatic environments such as deep ocean thermal vents, hot springs and deep petroleum reservoirs. Microbes have also been found in acid rock drainage as low as pH 1 or alkaline soda lakes in Africa and other parts of the world as high as pH 11. Microbes have also developed genes coding for the resistance to these toxic or extreme environments through an evolutionary process that may have taken many millions of years. Some researchers believe that theses extreme environments are more characteristic of the earth when life first began.

These extreme environments can provide sources of both microbes and their genetic information that can be transferred into the appropriate microbes that are capable of functioning in the extreme environment of an oil reservoir. In the case where a petroleum reservoir contains indigenous microbes that are detrimental to oil recovery (light oil degraders) the salt concentration could be adjusted to a salt level that is toxic to the indigenous microbes but is still within the preferred range of environmental conditions favorable to the engineered strain. This adjustment can be by waterflooding with a fluid as part of the oil recovery process. Therefore, the selection of halophilic microbes for use in oil recovery is the basis of this method. This invention provides methods of developing a culture of microbes that will carry out an oil recovery process without the unwanted consumption of short chain alkanes. In prior methods of MEOR, by simply stimulating the indigenous microbes in petroleum reservoirs the consumption of short chain hydrocarbons could cause reduction in oil viscosity.

High salt environments can be inhabited by halophilic microbes from both domains; bacteria and Archaea. Aquatic environments can be variable in salt concentration or consistently high in salt. Halotolerant (high salt concentration tolerant) microbes can inhabit both variable and consistently high salt aquatic environments. These are different than true halophilic microbes (salt-loving) that inhabit only consistently high salt environments. Currently there are about a 100 microbes that have been isolated and studied from high salt environments.

Microbes that can live in a salt water environment have adapted to the high osmotic pressure by using two different mechanisms. In the first process, the cell responds to an increase in salt or a drop in water concentration outside of the cell membrane by making small organic molecules. These small organic compounds will reduce the water concentration inside the cell to equal the outside concentration. In the second mechanism, the high salt concentration (low water concentration) of the extra cellular environment is balanced by an equally high ionic salt concentration (generally potassium chloride) within the cytoplasm. This is referred to as the "salt-in" adaptation. This salt-in adaptation requires major changes to the structure of internal proteins and other compounds in the cytoplasm of the cell. Microbes that have adapted to high salt by this mechanism are obligate halophiles and are unable to survive in a low salt environment.

The halotolerant bacteria make use of the small organic molecule mechanism to balance the osmotic pressure. *Bacil-* lus licheniformis JF-2 (ATCC 39307) is an example of a microbe that is used to produce surfactant for MEOR and is halotolerant up to 8% NaCl (1.4 M NaCl). Their cytoplasmic water content is reduced by soluble organic molecules to match the low water content of the external salt water environment. However, they use large amounts of energy to produce organic molecules that balance the osmotic pressure that is created by the high levels of salt in the environment. The halo-tolerant bacteria do not maintain high cytoplasmic salt levels because their intracellular proteins do not function in high salt. The use of organics to balance the osmotic pressure gives them an advantage in a changing salt concentration environment. They can secrete small organic osmotic balancing molecules quickly if the environmental salt concentration decreases. In addition, this type of salt tolerance has another advantage for the microbe. It does not require changing a large number of the cell's proteins to adapt to changes in the salt concentration. For a microbe to become salt tolerant it needs to acquire genes that code for the production of the small organic osmotic balancing molecules. These can be transferred by natural horizontal gene transfer. However, this advantage comes with a great energy cost needed for the production of the organic molecules that balance the external salt concentration.

(3) Obligate Halophiles

The first reported discovery of an obligate *halophile* was made by Volcani for his Ph.D. thesis in 1940. The halophilic Archaea were isolated from the Dead Sea where they can exist at over 10 million cells per ml. It was also discovered that these microbes could not grow in less than 1.5 M salt, which is about twice the salt concentration of sea water. After more than 30 year of research on these unusual microbes, a new domain of life known as the Archaea was proposed. Haloarchaea became model organisms and were the first Archaea to be genetically transformed. Currently there are 7 haloarchaeal genomes listed on the University of Maryland website (halo4.umbi.umd.edu/). In addition to haloarchaeal obligate haplophiles, there are bacteria that have evolved the same mechanism of maintaining a high ionic cytoplasm. Currently 4 obligate halophilic bacterial genomes have been sequenced. Analysis of the proteomes of both the bacterial and haloarchaeal homologous enzymes have shown evidence of convergent evolution and LGT which has led to similarities in amino acid residues common to obligate halophiles. It is therefore possible to make predictions of modifications or mutations to non-halophilic enzymes that would render them more soluble and functional in an obligate *halophile* cytoplasm.

Normally the proteins and other molecules that make up microbial cells will not function at a high salt concentration. In order for enzymes and other compounds within the cytoplasm of a salt-in *halophile* to function in the high ionic solution there must be changes made to the surface charges. Proteins can be altered in their number of basic and acidic amino acids that will make them more stable to high ionic solutions. For these microbes to have had to adapt to this different cytoplasmic salt concentration they must have undergone significant changes to the amino acid composition of their proteins and consequently the gene sequences that code for them. Analysis of the genomic sequences of these obligate halophiles from both archaeal and bacterial examples indicate an increase in the number of acidic amino acid residues and in particular aspartic acid and a decrease in basic amino acid residues (in particular lysine). In addition to an increase in the number of acidic amino acid residues on the surface of the halophilic enzymes, there is generally a decrease in the number of hydrophobic amino acid residues, which leads to a more flexible protein.

Changing one base pair of a three base pair codon is a single mutation and will not result in a charge change of the amino acid it codes for. Changing from a lysine to an aspartic acid requires a change in two bases in the codon (Lys, AAA or AAG to Asp, GAU or GAC). To make a change this radical, from a basic to acidic amino acid, requires a double or triple mutation of the codon's base pairs. These radical changes are the type found in homologous proteins as seen in the comparison of *halophile* to non halophiles or halotolerant microbes. They are unlikely to occur from simple point mutations, which would not result in such large charge differences. Therefore, this type of adaptation would be extremely slow and not likely to occur in a species for many years.

Adaptation is unlikely to occur as a result of simple horizontal gene transfer from a non-halophilic microbe into an obligate *halophile*. Genes from non-halophiles or from low salt cytoplasm halotolerant microbes must first be modified so that the proteins they code for will be stable to high salt concentrations. This key feature of the salt-in or obligate halophiles can be the basis for a means that prevents the unwanted gene transfer from most other bacteria. If the indigenous is moderate in salt concentration, the genes from other indigenous microbes in the petroleum reservoir will not function in an obligate *halophile*. If an underground oil reservoir contained a large population of microbes that could metabolize the light weight oil these unwanted genes could not be picked up by the engineered obligate halophilic microbe. To be functional the indigenous genes would have to go though major changes so that they would be functional in the high ionic cytoplasm of the salt-in *halophile*. Generally, oil reservoirs that are either low in salt concentration or are subject to variation in salt concentration would be unlikely to contain microbes that could contribute functional genes to obligate halophiles.

In the special case, where an oil reservoir was high in salinity and contained indigenous halophilic microbes of the salt-in mechanism type and that also had genes that coded for light chain alkane degradation enzymes, LGT could potentially be a problem. In this case, these microbes should be killed off and eliminated from the reservoir before introducing the high salt culture selected or engineered for oil recovery. One method of eliminating indigenous halophiles is by fresh waterflooding of the reservoir. Generally obligate halophiles will not survive an exposure to water as low in salt as sea water. In addition, various toxic chemicals or biocides could be added to the low salt water-flood to help eliminate indigenous microbes that could function at high salt and that could consume short chain hydrocarbons. After the reservoir is cleared of indigenous high salt microbes, the engineered short chain alkane deficient culture can be added with controlled salt concentration water-flood fluid.

In certain embodiments of the present invention, new genes are added to a host halophilic microbe. After a microbe is selected for use in a high salinity reservoir it may be desirable to add genes for the degradation and use of high molecular weight hydrocarbons and/or the production of surfactants and polymers. If these genes are transferred from other non-obligate halophiles it may be necessary to modify the genes for high expression and function of the encoded enzymes in a high salt environment. This can be done by a combination of rational protein sequence design and site directed mutagenesis. Therefore, the proteins and enzymes required for the production of a surfactant or a hydrocarbon cleaving enzyme useful for oil emulsification, can be engineered into a true *halophile* after the gene sequences are changed to make the proteins more functional at high ionic salt concentrations.

Madern, D. et al *Biochemistry* (2000) 39: 1001-1010 reported on the structural differences of both malate and lactate dehydrogenases found in haloarchaea. Later, Ebel, C. et al in *Biochemistry* (2002) 41: 13234-13244, reported on solvent interactions of halophilic malate dehydrogenase. A recent comparison of amino acid use differences between obligate halophiles is provided by Sandip Paul et al. in *Genome Biology* 2008 9:R70. From analysis of these model enzymes found in both obligate halophiles, mutations can be made to genes isolated from non-halophiles so that those genes will be expressed in halophiles at high yield and will be functional at high salt. Also a number of these mutations can be evaluated for expression and enzymatic functionality in a *halophile* such as *Halobacterium* sp. NRC1 or *Haloferax volcanii* using molecular genetic tools such as the "pop-in-pop-out" method reported by Bitan-Banin et al., 2003 *J. Bacteriol* 185: 772-778 or Wang, G. et al., (2004) *J. Bacteriol* 186: 3187-3194.

In accordance with the present invention, if needed, the proteins and enzymes required for the production of a surfactant or a hydrocarbon cleaving enzyme useful for oil emulsification are engineered into a true *halophile* after the gene sequences are changed to make the proteins more functional at high ionic salt concentrations. The mutated sequences are evaluated for expression and activity in a high salinity environment. In addition, the engineered halophilic microbes will not acquire the light oil consumption genes from the indigenous microbes existing in the reservoir, because the proteins encoded for are functional in the low ionic cytoplasm of a halotolerant microbe and are unlikely to function in the high salt cytoplasm of the engineered "salt-in" *halophile*.

The "salt-in" obligate halophiles cannot tolerate a drop in salt concentration, unlike the halotolerant bacteria which can quickly adapt by secreting small organic molecules, like glycerin as the salt level changes. In many cases, even a drop down to the concentration of sea water is enough to destroy the cell wall and kill the "salt-in" microbes. Even a slow adjustment over years would kill off the true halophiles because of the huge changes in gene sequences that would be required. Therefore, halophilic salt-in microbes have an advantage in that they can thrive in a high salt environment without undue energy requirement for maintaining osmotic pressure, if the salt concentration docs not drop below the toxic limit for the halophiles.

Therefore, a halophilic Archaeon is a good host microbe to engineer for oil reservoirs that can be maintained at high salt concentration at all times. It has a competitive advantage because it does not need to produce large amounts of small organic molecules to balance the osmotic pressure. Also, the engineered microbes can be readily killed by reducing the salt concentration of any process solution before leaving the site. As an added benefit, this has a regulatory advantage in meeting EPA requirements under Toxic Substances Control Act (TSCA) on both release and survival in the open environment. The details for method of containment and requirements for the proper disposal are published in the Federal Register of Apr. 11, 1997.

Conversely, halotolerant microbes are preferred if the process were expected to encounter changes in the salt concentration. The halotolerant engineered microbes will be able to tolerate changes and fluctuations in salt levels which can be used to kill off true halophiles that might interfere with the engineered microbes. In that case, the halotolerant culture needs to be maintained on a preferred carbon source to provide enough energy and carbon for salt resistance.

Examples of Halophilic Microbes

The first genome of a "salt-in" halophilic Archaea, *Halobacterium* sp NRC-1 (NC_002607, NC_002608 and NC_001869), was completely sequenced in 2000 (L. Hood et al PNAS 97 pp 12176-12181). It became a model microorganism to study. Although it is an aerobic mesophilic Archaeon, its ease of culturing and the ability to manipulate and replace genes make it a good host or gene recipient microbe to develop a laboratory model for expression of surfactant and bio-polymers useful in oil recovery at high salt. It has a 2,571,010 bp genome that codes for 2,630 predicted proteins, many of which have known or predicted functions. Since then, the genomes of at least five more of the "salt-in" halophiles have been sequenced. Their genomes and proteomes compared to some other non halophiles by Sandip, Paul, et al. in Genome Biology 2008 found online at (genomebiology.com/2008/9/4/R70). These well studied extreme salt loving organisms could serve as a host microbe to engineer for the production and secretion of useful metabolites that would emulsify and aid in the recovery of oil from petroleum reservoirs.

Halophiles may be isolated from oil reservoirs. A typical oil reservoir can be not only high in salt, but low in oxygen and at elevated temperatures. The host *halophile* should be chosen to use an alternate electron acceptor such as nitrate and be able to grow at 40 to 80 degrees Celsius. These microbes would be found in high salt environments that were also deep or low in oxygen and at high temperatures. Deep oil reservoirs that are high in salt is a likely environment to isolate useful microbes from that could be engineered into producing useful oil recovery metabolites without consuming oil. Needed genes such as the ability to grow on a singles carbon source could be added if the microbe lacked them.

*Halobacterium* sp. R-1 (NC_002607, NC_002608 and NC_001869), is an extreme *halophile* similar to *Halobacterium* sp. NRC-1. Its 2.8 Mbp genome was completed in 2008.

*Haloferax volcanii* (NC_013967), is a moderate *halophile* isolated from Dead Sea mud. It grows optimally, with a generation time of about 4 hours in rich medium containing 1.5-2.5 M NaCl at 45 degrees C. It requires at least 0.02 M Mg and is tolerant of up to 1.5 M Mg. It can grow more slowly in minimal medium with glucose as a single carbon source. It genome was completely sequenced in 2006. *Halofexax volcanii* is widely used for genetic experimentation as is *Halobacterium* sp. A more detailed description of this microbe is given by Berquist, Muller and DasSarma in Method in Microbiology Vol. 35: 649-679.

*Haloarcula marismortui* (ATCC 43049), is an Archaeon metabolically versatile and an extreme *halophile* from the Dead Sea. It has a 4.3 Mbp genome that was completely sequenced in 2004.

*Haloarcula quadrata*, (in culture collection as AB010964, AB010965, DSM11927) growth in 2.7 to 4.3 M NaCl, pH 6.5 to 7.0, optimum temperature 53 deg. C., anaerobic growth on nitrate, growth on a single carbon source. This culture was isolated in Sinai, Egypt. Ref. Oren et al. 1999, Int. J. Syst Bacteriol 49 1149-1155

*Halogeometricum borinquense* (in culture collection as AF002984 and ATCC 700274) growth in 1.4 to 5.2 M NaCl optimum range 3.4 to 4.3 M NaCl, pH 7 optimum temperature 40 deg. C. anaerobic growth on nitrate, growth on a single carbon source. Isolated from a saltern in Puerto Rico. Ref. Montalvo Rodrquez et al. 1998 Int. J. Syst. Bacteriol. 48: 1305-1312.

*Haloferax denitrificans* (in culture collection as ATCC 35960 and DSM 4425) growth in 1.5 to 4.5 M NaCl optimum range 2 to 3 M NaCl, pH 6.7 optimum temperature 50 deg. C. anaerobic growth on nitrate, growth on a single carbon source. Isolated from a saltern in California USA. Ref. Tomlinson et al 1986 Int. J. Syst. Bacteriol. 36:66-70

*Haloquadratum walsbyi*, is a square shaped extreme *halophile* isolated from solar salterns with a 3.2 Mbp genome that was sequenced in 2006.

Alkaliphilic Archaeal Halophiles:

Alkaliphilic halophiles can be found in hypersaline soda lakes such as Lake Magadi in Kenya, Wadi Natrum lakes in Egypt and soda lakes in China. These could be engineered to produce bio-surfactants and other biological oil recovery compounds that were effective at alkaline pH. Generally alkaline pH is better for oil emulsification. Increasing the pH of the flood water can be done by adding caustic soda and would have the added advantage of suppressing the growth of endogenous microbes that might interfere or have detrimental effects on the quality of the oil produced.

*Halothermothrix orenii* is an anaerobe isolated from a Tunisian salt lake that grows in 3.4 M NaCl (20% salt) at 68 deg. C. Ref. Cayol J-L et al 1994 Int. J. Syst. Bacteriol. 44: 534-540.

*Natronobacterium magadii* and *N. gregoryi* are alkaliphilic halophiles but, not thermophiles that have been isolated from Lake Magadi in Kenya (ref. Tindall et al 1984 ATCC 43099 and 43098). They have a pH optimum of 9.5 and a salt range of 2.0-5.2 M NaCl.

*Natronomonas pharaonis* (NC_007426, NC_007427, and NC_007428), is an alkaliphilic extreme *halophile* isolated from a soda lake. This Archaea's 2.6 Mbp genome was completely sequenced in 2005.

Bacterial Halophiles:

*Salinibacter ruber* (NC_014028, NC_014030, NC_014032), is an extreme *halophile* with a 3.6 Mbp genome that was sequenced in 2006.

*Chromohalobacter salexigens* (NC_007963), is a moderate *halophile* that survives on a variety of salts. Its 3.7 Mbp genome was sequenced in 2006.

*Halothermothrix orenii* (NC_011899), is a thermophilic bacterial *halophile* with a 2.7 Mbp genome sequenced in 2006. This bacterium was isolated from sediment of a Tunisian salt lake and grows optimally from 50 to 100 g per liter NaCl at 60 degrees C.

*Halorhodospira halophile*, is a bacterial extreme *halophile* that can oxidize sulfur. Its 2.7 Mbp genome was sequenced in 2007.

In addition to the microorganisms listed above, a larger list is provided by Enache, M. et al. in the International Journal of Systematic and Evolutionary Microbiology (2007), 57:2289-229, which is expressly incorporated by reference herein. In addition to the *halophile* listed above other halophiles can be selected from culture collections or isolated from high salt environments.

Further details of the invention are provided in the following non-limiting examples.

All references cited throughout this disclosure and the references cited therein are expressly incorporated by reference herein.

EXAMPLES

Example 1

Step 1: Microbe Isolation, Characterization and Improvements: Site Selection:

Environments of consistently high salt concentrations (salinities exceeding 100,000 ppm total dissolved solids) are best for isolation of obligate halophiles. Sites also containing liquid hydrocarbons such as petroleum oil fields or waste oil/brine disposal pits are good candidates for microbes that are both halophiles and also have the ability to metabolize various types of hydrocarbons. Microbes selected for use in MEOR should be able to function in a low oxygen environment. Facultative anaerobes are ideal host microorganisms. Especially good are microbes that can use nitrate as an election acceptor. Aerobic microbes may be used in applications where large amounts of air can be injected with the waterflood fluid. Microbes isolated from these environments can also be a source of genes and gene sequence information that can be used to genetically modify a culture of microbes, which can be tested and used on oil reservoirs of high salinity or where brine is used as waterflood.

In one example, following the method described by S. Kebbouche-Gana, et al., reported in the *J. Ind. Microbiol. Biotechnol.* 2009 36:727-738, isolating five strains of Halobacteria or Haloarchaea that were able to produce bio-surfactants, samples are collected at 1-m intervals from a high salinity pond. The microbial isolates are cultured in a standard medium containing 125 g of NaCl, 160 g of $MgCl_2$ $6H_2O$, 5.0 g of $K_2SO4$, 0.1 g of $CaCl_2$ $2H_2O$, 1.0 g of yeast extract, 1.0 g of casamino acids and 2.0 g of soluble starch. The pH is adjusted to 7.0 with NaOH. This medium is also increased to 3.5M NaCl (203 g/l) and 5% v/v diesel oil. Cultures are grown at 40° C. with shaking at 200 strokes per minute. Various carbon sources such as glucose, fructose, arabinose and sucrose are tested by omitting starch and reducing yeast extract and casamino acids to 0.25 g/l. Growth is monitored by optical density at 600 nm. The pH of each culture is determined and a drop in pH to below 6.0 is considered evidence of acid production.

Surfactant production is monitored by a drop in surface tension. Screening of colonies for surfactant production is performed by the qualitative drop-collapse test described by Jain et al. (1991) *J. Microbial Methods* 13:273-280. Two microliters of oil are applied to well regions delimited on the covers of 96-well microplate (Biolog, Hayward, Calif.) and left to equilibrate for 24 hours. The oil used for the test can be motor or petroleum oil characteristic of the intended reservoir for MEOR. A liquid sample is removed from each of the isolated strain cultures after 7 days of incubation. After centrifuging for 5 minutes at 12,000 g to remove cells, 5 microliters are added to the oil coated well regions. The drop size is observed after 1 minute with the aid of a magnifying glass and compared to a sterilized negative control. A drop diameter at least 1 mm larger than the control is considered an indication of surfactant production. The positive isolates are further evaluated for oil emulsion-forming ability and emulsion stability.

Surface tension reduction depends on the chemical and physical conditions such as temperature, salinity and pH. For laboratory testing these conditions should be tested over the range that is expected for an oil reservoir. For evaluation of chemical surfactants, a simple lab scale test was developed by Larry W. Lake, (from a course, "Fundamentals of Enhanced Oil Recovery", at the University of Texas). This test can be modified to evaluate the effectiveness of surfactant for EOR. For the modified test, a number of tubes are filled with equal volumes of oil (ideally the petroleum oil that is typical of the reservoir to be treated with MEOR) and an aqueous phase that represents the fluid to be used as the waterflood buffer. The salinity, temperature and pH can be varied over a range that would be economical at a commercial scale for a waterflood fluid used as part of the process. To the aqueous fluid, various size aliquots of cell suspensions are added to each tube experiment. It is best to use cells that are in exponential growth phase, or are at a phase when surfactant production is high. The tubes are vigorously shaken and left to form emulsion layers. After several hours the middle layer between the top oil layer and the bottom aqueous layer is measured. The larger the middle layer, the better the aqueous fluid, which contains microbes and the surfactants they make, is at reducing the interfacial tension (IFT) and the better it will be at improving oil production. These results can be tabulated to identify the best microorganism strain in terms of size of middle layer per unit of cells or volume of cell broth. The selection of the best strain will depend on the physical and chemical condition of the fluid used as a waterflood buffer. Some strains may be best for high salinity fluids and others may be best at lower salinity fluids. The selection of chemical and physical conditions will depend on economic and environmental limitations of the petroleum reservoir.

Bio-consumption or utilization of the hydrocarbon liquid added to the media is often linked to the production of surfactant. That is because microbes that metabolize oil will often make surfactants to aid in the uptake of oil. Microbes that produce surfactant are also likely to express high levels of enzymes that are needed for the degradation of liquid petroleum. Ideally one would like to find a microbe that could produce surfactant without also consuming oil, especially the short chain alkanes. This is difficult because the genes for both oil consumption and surfactant production are generally clustered together and controlled by the same promoter. However, the genetic information contained in microbes, that have the capability of doing both, is useful. Knowing the sequence of the genes that code for monooxygenases, which are generally the enzymes that start the alkane metabolism, is useful information for the modification or elimination of the short chain alkane metabolizing capabilities.

Step 2: Isolation of DNA and Genes Needed for Surfactant Production and Liquid Oil Consumption Microbial strains selected for high and effective surfactant production can be further characterized by gene sequencing. DNA is extracted from poly-carbonate filters as described by Minz et al. (1999) *Appl. Environ. Microbiol.* 65: 4666-4671. This procedure was modified by Kebbouche-Gana et al. The DNA was electrophoresed, excised from the gel and purified with a jet sorb gel extraction kit (Genomic DNA purification system PROM, EGA). Purified DNA from selected strains are amplified with specific 16s rRNA archaeal primers (5'-TCCGGTTGATCCYGCCGGA-3'(SEQ ID NO: 1) and 5' YCCGGCGTTGAMTCCAATT-3' (SEQ ID NO: 2)). 16s rRNA sequence information can be aligned with rRNA sequence from known Halophiles for genera and family identification.

DNA or mRNA probes can be based on known genes from an organism that produces a surfactant. One example is *Pseudomonas aeruginosa*, which produces rhamnolipid. The synthesis of this glycolipid is by sequential glycosyl transfer reactions. The genes involved in rhamnolipid biosynthesis are encoded on a plasmid, and their expression is regulated by a quorum sensing system. A more complete review is given in Lang and Wullbrandt (1999) *Appl. Microbiol. Biotechnol.* 51:22-32. Other species, such as *Bacillus subtilis*, produce surfactin, a lipopeptide which contains about 7 amino acid residues. Other microorganisms secrete higher molecular weight biosurfactants consisting of polysaccharides, lipoproteins, and lipopolysaccharides. Isolation and identification of the surfactants secreted by the isolated strains can be done by HPLC with a mass-spec detection system. Identification of the chemical nature of the surfactants produced by each isolated strain can be useful information for finding genes that are required for the surfactant production and secretion. For example, a glycolipid similar to rhamnolipid would likely be dependent on genes similar to those involved in its biosynthesis in *P. aeruginosa*. These genes from well characterized microbes can be used to construct probes for finding similar genes in the halophilic isolates.

However, even if the surfactants produced by the halophilic microbes are completely new and unlike any other well studied surface active compounds, other methods of gene isolation can be used. For example, correlating higher levels of mRNA with production of high levels of surfactant can be used to find needed genes. If the presence of alkanes induces the production of surfactant, than the level of mRNA needed for surfactant production will be increased. The use of DNA microarrays can identify the increase in gene transcription into mRNA when surfactant production is induced. Sequencing of the cDNA made from the increased mRNA can be used to identify the required genes sequences.

Based on this method, the identification of genes required for the production of surfactant production and the degradation of liquid oil can be done by mRNA differential display. This method was used to identify Cyclohexonone metabolism related genes (Brzostowiez et al. (2000) J. Bacterial. 182: 4241-4248). These mRNA techniques make it possible to access regulated genes directly without purification of gene products. These approaches are based on comparisons of two cultures and the identification of genes whose mRNA is more abundant when a metabolic pathway is induced. In the above example, if surfactant production is induced by the presence of oil, then mRNA that codes for surfactant production as well as enzymes for oil metabolism will be at higher levels compared to the uninduced culture. These techniques rely on the hybridization of DNA on membranes as described by Chuang and Blattner 1993 *J. bacterial.* 175: 5242-5252. It was by this method that Brzostowiez et al. that led to the discovery of the genes for two monooxygenase enzymes responsible for the oxidation of cyclohexanone. This same technique can be used for the identification of genes coding for proteins and gene products of halophilic archaea that lack enough sequence homology to bind to probes constructed based on protein sequence of non-halophilic or mesophilic homologous enzymes.

Probes may also be based on protein sequence of homologous enzymes with highly conserved catalytic site and binding sites. In this case a short degenerate DNA probe is constructed to bind with any DNA that has the sequence of base pairs that code for the highly conserved amino acid residue sequence.

Although all these method can be successful at isolating new genes required for surfactant production and liquid hydrocarbon oil degradation in halophiles, as more gene sequences are obtained from obligate halophiles the faster the isolation of new genes is accomplished.

Step 3: The Prevention and Modification of Short Chain Alkane Metabolism:

The expression of genes required for the production and secretion of surfactants and the degradation of high molecular weight hydrocarbons are beneficial to the mobilization of oil. It is the degradation of short chain alkanes and other low viscosity petroleum components that is very detrimental to oil recovery. Therefore, if the genes of a microbe could be modified so that they do not metabolize light oil, the viscosity would decrease and recovery of petroleum would increase. However, this must be done in such a way that production of surfactant, which may be under the control of a single gene promoter, is not also prevented. With the loss of liquid oil metabolism, another utilizable carbon source is needed to offset the loss of energy from the light chain hydrocarbon metabolism. Often the genes needed for both liquid hydrocarbon consumption and surfactant production are clustered together. Therefore, deactivating or removing the genes needed for short chain alkane uptake must be done in such a way that the genes needed for high production of surfactant are not deactivated or down regulated.

One method of achieving this specific gene modification is homologues gene replacement. A new gene replaces a similar wild type gene with a modified nucleotide sequence that codes for a protein with a different amino acid sequence. This process can be used to make small changes to enzymes to change the catalytic efficiency or specificity of the enzyme. A change of one or two amino acid residues can make the new enzyme no longer able to bind the same substrate or catalyze key steps in the conversion of substrate to product at the same rate. This process has been used in many genetic systems wherein similar genes are replaced by mutated and by homologous recombination (Molecular Biotechnology edited by Glick and Pasternak, 2003, Chapter 8). Along with the mutated gene, a selectable maker is also incorporated so that new microbes that have taken up the mutated gene can be selected. This process requires a certain level of genetic manipulation tools. Fortunately, a gene knockout system has been developed for the halophilic Archaea, *Haloferax volcanii* and *Halobacterium salinarum* based on the pyrE gene reported by Bitin-Banin et al. in *J. Bacteriol.* 2003, 185: 772-778. This system has been further developed and now four different selection principles are available (Allers et al. *Appl. Environ. Microbiol.* 2004, 70: 943-953) for *Hf. valcanii*. By using this technique or similar gene replacement techniques with selectable makers, the monooxygenase genes isolated from the wild type halophiles can be replaced with modified genes sequences.

By this process or other genetic manipulation processes a number of changes can be made in the amino acid sequence of enzymes that facilitate the uptake or metabolism of light chain alkanes. This process can be done by random changes to any amino acid in the enzymes sequence, by trial and error. The resultant enzymes with the amino acid changes can be tested for changes in substrate binding, substrate specificity and conversion to product rate. In general, most of the random changes will have little effect, or will decrease the catalytic rate. This process is much easier if the three dimensional structure of the enzyme is known or can be determined by X-ray crystallographic analysis. In this example the structure of some alkane specific monooxygenases have been determined and are useful in predicting key amino acids to change. For example, by making point mutations of the amino acid residues at the binding sites also known as histidine boxes, it would likely prevent or cause a reduction in the rate of alkane metabolism.

Changing any of the amino acid residues, especially the histidines, will affect the ability of these enzymes to metabolize liquid hydrocarbons. A number of these modified enzymes can be evaluated in a model halophilic host such as *Haloferax volcanii* to determine the enzymes ability to function at high salt. Modified wild type halophiles with the mutated alkane conversion enzymes can be evaluated at the laboratory scale for their ability to produce surfactant, but with limited ability to grow on octane or diesel as a carbon source. From the group of engineered microbes, the strains that achieve high levels of growth with an inexpensive carbon source, and that produce high levels of surfactant, and that consume the smallest amount of light molecular weight oil (C6-C8) are selected. The consumption of short chain alkane can be determined by analysis of remaining oil in the reaction vessel. A more sensitive method is with a carbon 14 isotope labeled alkane. Small amounts of uptake of the isotopic carbon can be measured in the cells. Alternatively, the rate can be determined from the isotopic carbon dioxide produced.

From this group of engineered microbes the selected halophiles are tested for their ability to mobilize oil in a laboratory scale waterflood core sample test. This test consists of saturating a reservoir rock core sample or a packed sand column with petroleum oil. A flow of water or brine is then pumped through the core sample until the free oil is washed out. Then the microbe culture in a growth buffer is introduced into the core sample that still contains the residual oil. The core sample inoculated with microbes is left to incubate for one to two weeks. After incubation, a flow of waterflood buffer is passed through the core and the amount of removed oil by this flow is measured as a function of buffer flow volume. With this small scale laboratory, test the effectiveness of each of the engineered and wild type cultures can be measured and compared. The improved cultures should show an increase in the rate and total amount of oil removed from the core. There should also be an increase in the number of microbes, indicating growth in the high salt environment. However, this short test does not indicate oil or light chain alkane consumption because the time that the microbes are in contact with the petroleum is too short and there is no easy way to measure the total remaining oil.

Therefore, another approach is needed to determine the short chain alkane consumption. The conditions of the digestion should match the waterflood drive buffer or fluid. It should contain the soluble carbon source such as molasses that will be used to supplement growth. However, the soluble carbon source should not be a catabolite that will cause repression of alkane degradation pathway genes. A report of carbon sources that can cause repression of alkane degradation pathways in *Pseudomonas putida* is given by F. Rojo et al. in the *J. Bacteriology* 2003 185: 4772-4778. The incubation should be long enough (several weeks) to measure degradation and loss of alkanes or a change in total alkane hydrocarbon composition or a change to the relative amount of various hydrocarbons if a mixture or sample of petroleum oil is used. The measure of an engineered or selected microbe that will be a good commercial candidate is that there is no decrease, or relative decrease, in the lighter weight hydrocarbon. As a comparison, this same test is performed with the indigenous microbes isolated from the location or oil reservoir. A test using only the stimulation of indigenous microbes might produce less oil, or produce oil with a larger high molecular weight fraction. The best cultures will be the ones that can produce the most surfactant and the most oil without decreasing the percentage of light weight oil in the petroleum samples.

Example 2

In this example essentially the same procedure described in Example 1 is used to isolate halophiles that are able to grow in brine solution in an environment similar to an underground petroleum reservoir to isolate a strain that is able to utilize petroleum compounds of various types. If the strain of *halophile* isolated is capable of metabolizing both short and long chain alkanes, the gene for metabolizing short chain hydrocarbons is knocked out while maintaining the genes for longer chain alkanes. The ideal location for isolation of such halophiles is a petroleum reservoir with a brine solution of over 100,000 ppm of total dissolved solids. In addition the temperature should not be more than 80° C. so that the brine taken from the reservoir is likely to contain microorganisms.

There are a number of species of microbes that have been reported that only degrade high molecular weight oil. For example, Banerjee et al. in U.S. Pat. No. 5,013,654, isolated a strain of *Pseudomonas aeruginosa* SB-1 and a mutant strain SB-3 that could only grow on paraffins (alkanes) of 20 carbons or more. Feng et al. in *PNAS* Mar. 27, 2007 p 5602-5607 reported a non-*halophile* (*Geobacillus thermodenitrificans* NG80-2) that metabolized only alkanes over C15. This thermophile was isolated from a hot petroleum reservoir in China. However, there are very few reports of hydrocarbon degrading microbes that are also obligate halophiles.

Obligate halophiles that have the ability to metabolize higher molecular weight petroleum components are useful microorganisms to use for oil recovery in high salinity brine oil reservoirs or where high salinity solution is used as a waterflood fluid. In addition to being a good host microbe to engineer, these microorganisms also provide a useful source of gene sequence information for the modification of enzymes from non-obligate halophiles to remain soluble and function in the high salt concentration of an obligate *halophile*. Also, halotolerant microbes, that maintain osmotic balance with the production of small organic molecules, often maintain slightly higher cytoplasmic salt concentrations. Comparison of homologous protein sequences has shown that these halotolerant microbes have evolved minor changes to their proteins to accommodate the higher salt. The analysis of enzymes that catalyze the first step in the degradation of alkanes by halotolerant microbes such as a monooxygenase could provide insight into selecting amino acids for site directed mutagenesis to osmotically-adapt a monooxygenase to function in an obligate *halophile*. This sequence information, in combination with the three-dimensional structure information, can be used to engineer a mesophilic enzyme to function at high salt concentrations.

In the case where no high molecular weight alkane degrading halophilic microbes can be isolated, it is possible to modify and transfer a gene from a non-*halophile* or halotolerant microbe into a *halophile*. For example a synthetic gene can be constructed to express a halophilic enzyme to degrade long chain alkanes based on a protein sequence from a wild type non-*halophile* that can degrade long chain in lower salt environments. This can be done to replace a short chain monooxygenase gene like the one described in Example 1.

In a specific example, the wild type gene that codes for the long-chain alkane hydroxylase LadA isolated from *G. thermodenitrificans* NG80-2 (SEQ ID NO: 2 encoding polypeptide of SEQ ID NO: 3) is mutated to be more soluble in high salt and function at a salt concentration of over 1.5 M KCl, which is typical of an obligate halophilic cytoplasm. In this example; the LadA protein sequence, the binding sites and the crystal structure are reported by L. Li et al. in *J. Mol. Biol.* 2008, 376: 453-465. In this specific example, the LadA protein sequence was compared to other protein sequences in the protein data bank and found to be a flavoprotein monooxygenase that utilizes dioxygen to insert an oxygen atom into the substrate. Based on X-ray data and molecular replacement methods computer programs, Li and co-workers were able to report the crystal structure with enough resolution to produce a model of the LadA protein, the FMN coenzyme and the long chain alkane substrate complex. The binding cavity for the alkane is packed with hydrophobic amino acid residues which hold the 16-carbon or longer chain. The four polar residues, His17, Tyr63, Gln79, and His311 are located above the terminal carbon of the alkane to form the reactive site. Directed mutagenesis was done to show that these four amino acid residues plus Cys14 believed to be involved in a disulfide bridge holding the dimer together are all required residues for activity. To make the mutants, nucleotides were changed in the LadA gene to replace Cys14 with an Ala, His17 with a Phe, Tyr63 with a Phe, Gln79 with a Leu and His311 with a Phe in the protein. Each of the mutants was cloned into pET-28a(+) (Novagen, USA) with a 6× His tag at the N terminus and expressed in *E. coli* BL21 (DE3). Cells were grown at 37° C. in 1 l of LB medium containing 50 micro grams per ml kanamycin. Cells were grown to an $OD_{600}$ of 0.6-0.8, and were then continuously induced with 0.2 mM isopropyl-β-D-thiogalactopyranoside at 45° C. for another 4 h.

Protein isolation of each of the mutated enzymes that contained a single amino acid residue change was done by cell lysis and disruption and sonication followed by centrifugation at 15,000 g. The soluble supernatant was applied to a $Ni^{2+}$ chelating affinity column (1.5 ml of $Ni^{2+}$-NTA agarose) pre-equilibrated with 20 mM Tris-HCl (pH 8.0) and 10 mM NaCl lysis buffer. The contaminating proteins were washed off with 10 bed volumes of 20 mM Tris-HCl (pH8.0), 10 mM NaCl and 20 mM imidazole. The target protein was eluted with 20 mM Tris-HCl (pH 8.0), 10 mM NaCl, and 200 mM imidazole with about 15 ml of buffer. The protein was further purified by Resource Q anion-exchange and superdex-200 chromatography. The isolated proteins were assayed for activity by mixing with the long chain alkane substrate by the method described by Feng et al. with a modification. The reaction contained 50 mM Tris-HCl (pH7.5), 1 mM hexadecane, 1 mM each of $FMNH_2$ and $MgSO_4$, Remaining alkane substrate was measured by gas chromatography (GC). The wild type protein was used as a control. Li and co-workers reported that all the mutant LadA were inactive indicating that each of the five amino acid residues is needed for catalytic activity.

The same method of mutating one residue at a time followed by activity measurement, or a variant thereof, is used to adapt the long chain alkane hydroxylase to function in a high KCl environment. However, to adapt this enzyme to function at high salt concentrations each mutant should be assayed for activity at varying concentration of salt. For example, the rate of hexadecane conversion to hexadecanol should be assayed at; 100 mM NaCl, 100 mM NaCl and 200 mM KCl, 100 mM NaCl and 0.5M KCl, 100 mM NaCl and 1M KCl. Any mutation that reduces activity at low salt concentrations with no apparent increase in activity at higher salt concentrations is unlikely to be beneficial to osmotic adaptation. Mutations that do not decrease the rate of conversion at low salt concentration can be useful when combined with several other mutations, which add negative charges or reduce rigidity of the protein, to increase solubility and function at high salt.

The selection of amino acid residues to mutate for evaluation for osmotic adaptation is based on some general rules. The number of acidic residues should increase on the surface of the protein molecule. Halophilic proteins generally have a lower isoelectric point as a result of more acidic residues on the surface than their non-halophilic homologous proteins. The most common change is an increase in the number of acidic residues by replacement of Lys with Asp. Another way of reducing the isoelectric point is the insertion of a small domain or peptide that contains an excess of acidic residues. These changes and additions are to be performed on the amino acid residues on outer surfaces of the molecule or to peptide chains connecting domains. The addition of negative charges should not be at the hydrophobic binding pocket or at positions that are conserved as basic residues in homologous enzymes. Some possible changes to LadA to decrease the isoelectric point are listed in Table 1.

TABLE 1

| Amino Acid Residue in Lad A | Sequence Position of Residue in Lad A | Change to New AA Residue, a tested in mutant |
| --- | --- | --- |
| Lys | 48 | Asp, Glu |
| Lys | 50 | Asp, Gly |
| Lys | 170 | Asp |
| Lys | 195 | Asp |
| Lys | 204 | Asp, Glu |
| Lys | 263 | Glu |
| Lys | 266 | Glu |
| Lys | 267 | Glu |
| Lys | 276 | Asp |
| Lys | 287 | Glu |
| Lys | 295 | Ala |
| Lys | 301 | Gly, Ala |
| Lys | 322 | Asp |
| Lys | 343 | Glu, Asp |
| Lys | 357 | Asp |
| Lys | 358 | Glu |
| Lys | 415 | Asp, Glu |
| Lys | 419 | Glu |
| Arg | 262 | Glu |
| Arg | 264 | Gly |
| Arg | 413 | Ser |
| Arg | 423 | Ala |
| Arg | 432 | Ala |
| Arg | 434 | Val |

Another adaptation is a reduction in the number of large hydrophobic residues (Ile, Leu, Met, and Phe), which are replaced with less hydrophobic residues (Val, Thr). There is also an overall reduction in the number of disulfide bridges. All these changes should avoid key binding sites, reactive sites, important secondary structure determinates and conserved sequences. The goal of reducing the number of hydrophobic residues and the number of disulfide bonds is to make the protein molecule more flexible to function better in the high KCl concentration of the halophilic cytoplasm. All these changes can be tested by expression and analysis of the enzyme with substrate in various levels of salt concentration. It is possible that some changes will decrease the activity at low salt concentrations, but will keep it the same or increase the activity at higher salt concentrations. In the example of LadA, some changes that reduce the rigidity of the molecule are listed in Table 2.

TABLE 2

| AA Residue in Lad A | Sequence Position of Residue in Lad A | Change to new AA in Mutant |
| --- | --- | --- |
| Cys-Cys (bridge) | 168 & 214 | Ser, Ser |
| Cys-Cys (bridge) | 243 & 282 | Ser, Ser |
| Leu | 152 | Val |
| Leu | 171 | Val |
| Met | 277 | Thr |
| Phe | 278 | Thr |
| Ile | 281 | Thr |
| Met | 293 | Thr |
| Leu | 296 | Ala |
| Trp | 303 | Val |
| Leu | 305 | Val |
| Ile | 332 | Val |
| Ile | 337 | Val |
| Met | 341 | Val |
| Leu | 344 | Val |

In addition to changes in amino acids, halophiles also have changes in nucleotide use and GC-content of DNA. Accordingly, it is best to construct a synthetic gene based the abundance of GA, AC, GT and CG dinucleotides for stability at high salt concentration. The combination of several amino acid residue changes or the addition of an extra domain containing negatively charged amino acids can be coded for by a synthetic halophilic gene designed for expression in a model *halophile*. Some codons that are frequently found in obligate halophiles are listed in Table 3.

TABLE 3

| Codon Nucleotides | Amino Acid Residue |
| --- | --- |
| CGA, CGG | Arg |
| GUC | Val |
| ACG | Thr |
| CUC | Leu |
| UGU | Cys |

Two examples of model halophiles are *Halobacterium* species NRC-1 and *Haloferax volcanii* DS2. A detailed description of their genetic systems and methods for transformation is given by B. R. Berquist, J. A. Muller and S. DasSarma in *Methods In Microbiology* Volume 35 2006 Chapter 27. These model halophiles are well suited to express synthetic halophilic genes or wild type genes isolated from brine environments and likely to be halophiles. Procedures for expressing protein variants in *Haloferax volcanii* are described by Reuter and Maupin-Furlow in *Appl. Environ. Microbiol.* 2004, 70: 7530-7538 and is incorporated by reference. By these methods, mutations or added extra domain can be tested for expression and function in a high salt environment. In the above example, after a number of mutations have been evaluated and that are found to increase salt solubility without loss of activity, they can then be tested in various combinations for function in a halophilic expression system. Proteins adapted to function at high salt concentrations may not be soluble or active at lower salt concentrations. Therefore, in addition to expressing mutated enzymes in a model *halophile* it may also be necessary to isolate the protein in a high salt solution. This will require some changes to the protocol used by Li et al. to isolate mutations of LadA expressed in *E. coli*. These changes are likely to require adjustments to the binding and elution of the target protein from the Ni affinity column and the anion exchange chromatography. Gel filtration chromatography needs to be done at high salt so that the proteins do no aggregate or precipitate. Alternatively, enzyme activity can be tested without isolation of the enzyme by direct assay of the cell media to yield units of activity as a function of cell density. Quantifying of target protein can be done by gel electrophoresis.

After several of mutated forms of LadA are determined to be active at 1.5 M or higher KCl, the synthetic genes are transferred into the host *halophile* for evaluation as a microbe to aid in the recovery of oil. In one example, the host microbe is a *halophile* isolated from a high saline petroleum reservoir. The gene coding for the high molecular weight alkane degrading enzyme can be used to replace the homologous genes coding for the low molecular weight alkane degrader by homologous gene replacement with a selectable marker. The transformed cells are then selected and the marker removed. The transformed microorganisms are then grown under conditions of salt and temperature similar to the reservoir environment that will be used in for oil recovery. These microorganisms can then be evaluated in an oil saturated reservoir core sample test described above. In this test the surfactants and other compounds produced by the bacteria will dislodge a certain amount of oil over the buffer control. This test does not, however, reveal the benefit of having only high molecular weight petroleum degradation capability. To evaluate that, another test is needed.

To test the usefulness of the new microbe a mixture of short to long alkanes is digested by the mutant microbe and compared to a similar digestion by the wild type *halophile*. The conditions of the digestion should match the waterflood drive buffer or fluid. It should contain the soluble carbon source such as molasses that will be used to supplement growth. The incubation should be long enough to measure degradation and loss of alkanes or a change in total hydrocarbon composition if petroleum oil is used. The measure of a good or preferred engineered microbe is that it reduces viscosity. After digestion, there should be a relative increase in the lighter chain hydrocarbons and a reduction in the heavier or higher molecular weight oil components. This should result in a decrease in overall oil viscosity. The decrease in viscosity should also be compared to the results from the wild type microbe that still has the ability to metabolize short chain alkanes.

Microbes that can cause a decrease in overall viscosity, and that can still mobilize or dislodge oil as well as the wild type are then tested in an oil well field test. In a single well test, the microorganisms, along with nutrients similar to the culture collection medium used in Example 1, are pumped into a well that is at a salt level that is conducive for halophilic growth. The volume of liquid culture and nutrients should penetrate the reservoir for several meters beyond the well bore. This could be several hundred gallons or more. After penetration, the well is shut in with no more liquid pumped for two weeks. After the shut in period, the well is reopened and the amount of both oil and water removed from the well are measured. A successful MEOR microorganism will show an increase in the number of microbes, an increase in the amount of oil produced and a measurable reduction in the viscosity of the oil produced. As a control experiment, a similar test should be done by simple stimulation of indigenous microbes by just injecting nutrients into the oil well. As another control, test, another test with chemical surfactants should be run on the same well or similar well.

Example 3

In this example microbes are isolated for their ability to produce extracellular polymers in a high salt environment with little or no ability to consume light weight hydrocarbons. One of the most important factors for waterflood is sweep efficiency. Permeability variation and fractures will cause high flow of fluid through some areas and little or no flow in other areas. Polymers are useful in oil recovery because they can block the flow of fluid through the low resistance channels. They also thicken the water to make a better fluid to drive the oil out of the reservoir. Both bio-polymers and chemical polymers can be used for this purpose. Most chemical polymers are less effective at high salinity. Bio-polymers, especially those produced by microbes, which live in high salinity environments, are more useful for oil recovery from high salinity reservoirs. Bio-polymers are variable in their viscosity in high salinity brine. Pfiffner et al. reported in *Appl. Environ. Microbiol.* 1986, 51:1224-1229 isolating over 200 bacterial strains. The isolated strains can grow anaerobicly at 50° C. in up to 10% NaCl and could produce various levels of extracellular polysaccharides. The isolation media was Medium E also used by Jenneman et al. 1984, *Soc. Pet. Eng. J.* 24:33-37. The medium is a sucrose-mineral salts medium with 5% (wt/vol.) NaCl. Environmental samples were from a number of sources, most of which contented oil.

Unlike surfactant production, the genes required for extracellular polymer production are not necessarily under the control of the same promoter or clustered with the genes required for petroleum metabolism. However, most of the microorganisms used in MEOR have been isolated from oil rich environments or are the indigenous bacteria that live in an oil reservoir where the only source on carbon is oil. Although Pfiffner and co-workers were able to maintain both growth and polymer production on sucrose it is not clear that these isolated strains had lost their ability to metabolize petroleum hydrocarbons. Therefore, their use as either an inoculating microorganism or as an indigenous microbe could lead to loss of short chain alkanes and a corresponding increase in viscosity.

To prevent this from occurring, the isolation procedure should include a test for the ability of isolate to metabolize short chain alkanes. This can be done by microbiological techniques such as picking colonies that can grow on agar plates with a simple sugar carbon source, but that cannot grow on plates with a short chain alkane as the only carbon source. Alternatively, a radioactive or florescent probe to a gene that is characteristic of alkane degradation such as those described in Examples 1 and 2 could be used to screen isolate. Isolated microbes that grow well on a simple carbon source and produce high levels of polymer could revert back to consuming light oil if insufficient sugar were supplied.

To prevent polymer producing halophilic microorganisms from picking up genes from indigenous halophiles in a naturally high salt reservoir other genes could be added. For example, the modified gene that codes for the halophilic long chain alkane hydroxylase would give the polymer producing microbes an additional carbon source.

Ideally the production of polymers should be controllable. If bio-polymers could be produced in the high flow channels and high porosity regions it would force the flow of fluid into the unswept areas that were still retaining petroleum. Therefore having the genes that control the production of extracellular polymer under the control of an inducible promoter would be best. Certain levels of soluble carbon sources or metabolites may lead to increased polymer production. Identification of halophilic microorganisms that can only produce polymers when induced by certain metabolites such as xylose or arabinose would provide a means for control of polymer production. The induction of polymer production can be done after the reservoir is inoculated by starved or sporilated halophiles. Once in place, especially in the highest flow areas of the reservoir, the metabolite can be supplied by the waterflood fluid. This is expected to cause the most growth and production of polymer by the microbes that had infiltrated into the highest flow channels.

Therefore, the first step is selecting from many isolated halophilic the microbes that had the ability to: produce salt tolerant polymers, form spores, produce polymer only when supplied a certain group of carbon sources, grow without consuming short chain alkanes. The second step is to make sure that the selected microbes will not pick up or turn on a gene for short chain alkane consumption. The third step is to test the microbes in a field test of oil producing wells and water injection wells that is experiencing a problem with high flow zones causing the water flood fluid to by-pass much of the residual oil in place.

Example 4

A DNA construct for heterologous expression in *Haloferax volcanii* was synthesized that contained a modified version of the *Haloferax volcanii* HMG-CoA reductase gene promoter (Nuttall, et al., Biochem. J, 346(Pt 2) 251-254, 2000), a terminator adapted from the *H. volcanii* DNA gyrB gene, and a modified version of the *Aequorea victoria* Green Fluorescent Protein (GFP), known as smRS-GFP, containing four mutations, including Ser65Thr, Phe99Ser, Met153Thr, Val163Ala (the Phe99Ser, Met153Thr, and Val163Ala modifications confer the "soluble modified" protein properties; the Ser65Thr modification comprises the red-shifted mutation). The DNA construct was linearized by restriction digestion and ligated into pNG168, an archaeal/*E. coli* shuttle vector containing an archaeal origin of replication and a mevinolin resistance gene for selection in archaea (S. DasSarma, 1995).

*Haloferax volcanii* strain DS2 (ATCC 29605) was transformed with the pNG168-smRS-GFP plasmid, or pNG168, using established PEG-based transformation methods (Dyall-Smith, The Halohandbook: Protocols for Haloarchaeal Genetics, 2009), and transformants were selected on rich medium plates containing 2 μg/ml lovastatin (Tocris). After four days' growth at 46° C., transformant colonies were picked and patched to rich medium plates containing lovastatin and were grown overnight at 46° C.

The presence of the smRS-GFP gene in transformant *Haloferax volcanii* strains was confirmed by isolation of plasmid DNA from transformant *Haloferax volcanii* strains and DNA sequencing of the smRS-GFP gene. Transformant *H. volcanii* pNG168-smRS-GFP and pNG168 transformants were viewed under fluorescence microscopy. *H. volcanii* pNG168-smRS-GFP transformants exhibited strong fluorescence, demonstrating smRS-GFP expression, whereas pNG168 transformants did not.

Example 5

In a specific example of testing a modified LadA gene, for protein expression by an obligate *halophile, Haloferax volcanii*, a small number of lysine resides in the wide type LadA sequence were changed to codons that code for negatively charged amino acids. For expression of LadA, with an epitope tag comprised of six histidines (i.e., 6×His) at the protein N-terminus, wild-type LadA DNA sequence (*Geobacillus thermodenitrificans* NG80-2) was synthesized and cloned into pET-28a(+) (Novagen, USA; DNA 2.0, Menlo Park, Calif.). The resulting expression plasmid was transformed into BL21 *E. coli* (DE3) (New England Biolabs, Cat #C2527H) following the manufacturer's protocol, and the transformant strain was named GFF40.

Three DNA constructs for heterologous expression in *Haloferax volcanii* were synthesized that contained a modified version of the *Haloferax volcanii* HMG-CoA reductase gene promoter (Nuttall, et al., Biochem. J, 346(Pt 2) 251-254, 2000), a start codon followed by DNA sequences encoding an epitope tag consisting of six histidine residues at the N-terminus of following protein coding sequences, three different modified versions of the *Geobacillus thermodenitrificans* NG80-2 LadA gene, and a synthetic terminator sequence t.Syn (Allers, et al., Appl. Environ. Microbiol., 76(6): 1759-69, 2010). Of the three versions of the LadA gene, one version consisted of a DNA sequence codon optimized for expression, in *Haloferax volcanii*, of the published LadA protein sequence from *Geobacillus thermodenitrificans*. The two other versions of the LadA gene consisted of sequences identical to the first, except for changes at codons that specified changes at 3 amino acid residues (K263E, K267E, and K276D) and 5 amino acid residues (K263E, K267E, K276D, K357D, and K358E) in the published LadA protein sequence. DNA sequences for the protein coding sequences and terminator for the three DNA constructs, were synthesized (DNA 2.0, Menlo Park, Calif.) and PCR amplified using a reverse primer (prGFF32, SEQ ID NO: 12), matching terminator DNA sequence, and a long upstream primer (prGFF36, SEQ ID NO: 11), incorporating the entire HMG-CoA reductase promoter, to generate the final constructs containing promoter, protein coding sequence, and terminator. The PCR product was linearized by restriction digestion, and ligated into pNG168 (Allers T. and Mevarech M. Nature Reviews 6, 58-73, 2005 and Supplement and AY291460.1), an archaeal/*E. coli* shuttle vector containing an archaeal origin of replication and a mevinolin resistance gene for selection in archaea (DasSarma, S., in Archaea: A Laboratory Manual (eds DasSarma, S. & Fleischmann, E. M.) 241-252 (Cold Spring Harbor Laboratory Press, Cold Spring Harbor, N.Y., 1995), resulting in the generation of plasmids pNG168-LADA-wt-optHv1 (SEQ ID NO: 5), pNG168-LADA-mut3-optHv1 (SEQ ID NO: 6), and pNG168-LADA-mut5-optHv1 (SEQ ID NO: 7) (indicating plasmids harboring DNA sequences encoding the wildtype LadA protein (SEQ ID NO: 8), the LadA version incorporating three amino acid substitutions (SEQ ID NO: 9), and the LadA version incorporating five amino acid substitutions (SEQ ID NO: 10), respectively). DNA sequencing was carried out on resulting plasmids, verifying correct DNA sequence throughout DNA constructs and across ligation junctions within the plasmids.

*Haloferax volcanii* strain DS2 (ATCC 29605) was transformed with the three LadA expression plasmids, or with the original pNG168 plasmid, using established PEG-based transformation methods (Dyall-Smith, The Halohandbook: Protocols for Haloarchaeal Genetics, 2009), and transformants were selected on rich medium plates containing 2 μg/ml lovastatin (Tocris). After four days' growth at 46° C., transformant colonies were picked and transferred to rich medium plates containing lovastatin and were grown overnight at 46° C. Transformant strains were named GFF36, GFF31, and GFF22, for strains harboring pNG168-LADA-wt-optHv (Synthesized LadA with no mutated amino acids), pNG168-LADA-mut3-optHv1 (three mutated amino residues (K263E, K267E, K276D), and pNG168-LADA-mut5-optHv1 (five mutated amino residues (K263E, K267E, K276D, K357D, K358E)), respectively.

Cloning, Expression, and Purification

Synthesized wild-type native LadA was cloned into pET-28a(+) (Novagen, USA) with a 6×His tag at the N terminus and expressed in *E. coli* BL21 (DE3) (New England Biolabs, Cat #C2527H) following the manufacturer's protocol, and the clone expressed LadA named GFF40. GFF40 cells were grown at 37° C. in 100 mL of LB medium containing 100 μg/ml kanamycin, to an OD600 of 0.6-0.8, and were then continuously induced with 0.5 mM isopropyl-β-D-thiogalactopyranoside (IPTG) at 37° C. for a further 3 hours.

Transformations of *Haloferax volcanii* DS2 with mutated LadA were carried out by mixing 10 μL 0.5M EDTA (pH8.0) with 100 μL *Haloferax volcanii* competent cells gently and incubating for 10 minutes at room temperature. 1 μg pNG168 plasmid constructs was added to the cells/EDTA, gently mixed and incubated at room temperature for 5 minutes, followed by adding 110 μL 60% PEG (v/v) in unbuffered spheroplast solution (2 M NaCl, 17 mM KCl, 15% (w/v) sucrose], and incubated at room temperature for 30 minutes. Then 600 μL HV-YPC liquid medium was added to the cell solution, cells were recovered at 65,000 rpm for 5 minutes, and resuspended in 600 μL HV-YPC, incubated at 37° C. for 2 hours, plating on HV-YPC-agar plates, incubated the plates at 47° C. for 3 days. A 6×His-tag was added to the N-terminal of LadA of the LadA genes cloned. *Haloferax volcanii* (HV) transformant GFF31 (LadA hv3mut) controlled by over-expression promoter hv-HMG-CoA, *Haloferax volcanii* transformed with empty vector pNG168 (HVev), and *Haloferax volcanii* were grown at 47° C. for 20 hours. Cells were harvested by centrifugation at 4200 rpm for 10 min at room temperature. *E. coli* cells were resuspended in lysis buffer A [40 mM Tris-HCl (pH 8.0) and 10 mM NaCl], *Haloferax volcanii* were resuspended in lysis buffer B [40 mM Tris-HCl (pH 8.0) and 2 M NaCl], and disrupted by sonication, following centrifugation for 2 minutes at 14,000 g. The soluble cell lysate was applied onto a Ni2+-chelating affinity column (100 μL preequilibrated with lysis buffer). The contaminant protein was washed off with 1000 μL wash buffer [lysis buffer and 20 mM imidazole], and the LadA was eluted with 100 μL elution buffer [lysis buffer and 200 mM imidazole]. Eluted LadA from *E. coli* and *Haloferax volcanii* transformants were confirmed by gel electrophoresis followed by His-tag in-gel stain and coomassie blue stain.

Figure 3:
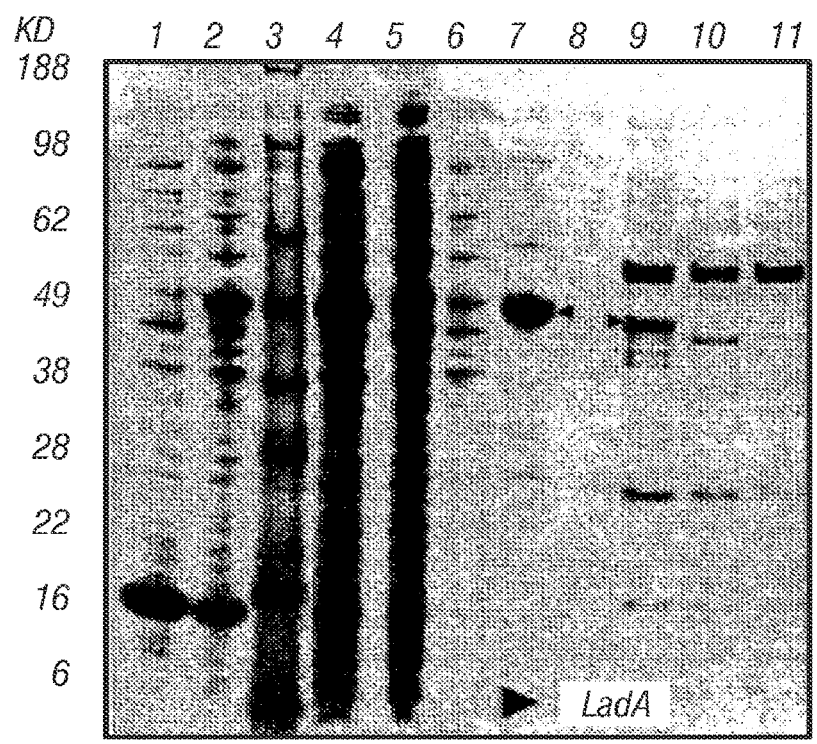
FIG. 3 is a photograph of a gel showing the expression of the ladA gene in *E. coli* and in *Haloferax volcanii*. NuPAGE 4-12% Bis-Tris gel (Invitrogen, Cat #NP0323BOX) analysis of Ni-NTA column purified native LadA (no amino acid residue change) from *E. coli* BL2 (DE3) (GFF40) and mut3 LadA (with 3 amino acids changed) from *Haloferax vocanii* (GFF31)

The results are shown in FIG. 3, which is a photograph of a gel showing the expression of ladA in *E. coli* and in *Haloferax volcanii*. The Novagen (now part of EMD) pET-28a(+) vector carries an N terminal 6His Tag, thrombin cleavage site (6 residues: Leu-Val-Pro-Arg-Gly-Ser), T7 Tag (11 residues, used for express studies using anti-T7 Tagantibody) and a few residues between these site/Tags, followed by multi-cloning site, thus give ~34 to 45 amino acids to the N-terminal of the expressed protein. For mutated LadA, the one we purified from HV has 7 residues added to its N-terminal (MHHHHHH-LadA).

Enzyme Activity Assays

Partially purified LadA *E. coli* and *Haloferax volcanii* transformants were assayed for alkane monooxygenase activity following the method described by Feng et al. (2007) with modification. The reaction mixtures contained 50 mM Tris-HCl (pH 7.5), 1 mM hexadecane, 1 mM each of FMNH2 and MgSO4, and variable amounts of each purified protein. A mixture without enzyme, a mixture with approximately equal amounts of eluted protein from *Haloferax volcanii*, a mixture with approximately equal amounts of eluted protein *Haloferax volcanii* transformant with empty vector pNG168, were used as controls. The mixtures were incubated at 60° C. for up to one hour before extraction with hexane. Aliquots of the hexane extracted long chain hydrocarbon substrate were analyzed by high performance gas chromatography. The hexadecane was eluted from a Agilent Technologies High performance capillary column 19091J-413 HP-5 (crosslinked 5% PHME siloxane) 30 meter 0.32 mm column. The gas chromatograph was a Hewlett Packard 5890 series II with a flame Ionization detector. The carrier gas was helium with a flow rate of about 15 ml per minute and a starting temperature of 120° C. which increased at the rate of 15° C. per minute until the final temperature of 280° C. was reached. Quantization and the determination of activity was done by comparison to injection and elution of hexadecane standard solutions and control digestions without added proteins. This method was used to determine if the modified proteins have equivalent activity to the wide type LadA and also to determine if the halo-adapted enzyme was active at higher salt concentrations than the wild type enzyme.

I claim:

1. A method of making a genetically engineered microorganism deficient in its ability to degrade short chain hydrocarbons of 12 carbons or less, comprising deleting, mutating or downregulating in an obligate *halophile* host microorganism able to grow in a salinity of about 5% or higher one or more genes that code for alkane hydroxylase enzymes capable of degrading said short chain hydrocarbons.

2. The method of claim 1, wherein the host microorganism is additionally able to utilize hydrocarbons of greater than 12 carbons.

3. The method of claim 1, wherein the host microorganism is additionally capable of producing surfactants.

4. The method of claim 1, further comprising the step of introducing into said host microorganism one or more genes required to utilize hydrocarbons of greater than 12 carbons.

5. The method of claim 1, further comprising the step of introducing into said host microorganism one or more genes required for the production of surfactants.

6. The method of claim 4, wherein said genes are placed under control of an inducible or constitutive promoter.

7. The method of claim 5, wherein said genes are placed under control of an inducible or constitutive promoter.

8. The method of claim 1, wherein the host microorganism is additionally able to utilize aromatic hydrocarbons.

9. The method of claim 1, wherein the host microorganism is additionally able to utilize hydrocarbons containing sulfur.

10. The method of claim 1, wherein the host microorganism is additionally able to utilize modified hydrocarbons containing nitrogen.

11. The method of claim 1, wherein the host microorganism is additionally able to produce extra cellular polymers.

12. The method of claim 1, wherein said host microorganism is an obligate *halophile* Archaeon or bacterium.

13. The method of claim 1 further comprising the step of introducing into said host microorganism one or more genes required for utilization of aromatic hydrocarbons.

14. The method of claim 1 further comprising the step of introducing into said host microorganism one or more genes required for utilization of hydrocarbons comprising sulfur.

15. The method of claim 1 further comprising the step of introducing into said host microorganism one or more genes required for utilization of hydrocarbons comprising nitrogen.

16. The method of claim 1 further comprising the step of introducing into said host microorganism one or more genes required for the production of extracellular polymers.

* * * * *